US011561197B2

(12) United States Patent
Aran et al.

(10) Patent No.: US 11,561,197 B2
(45) Date of Patent: Jan. 24, 2023

(54) ELECTRONIC DETECTION OF A TARGET BASED ON ENZYMATIC CLEAVAGE OF A REPORTER MOIETY

(71) Applicant: AMMR Joint Venture, La Jolla, CA (US)

(72) Inventors: Kiana Aran, Pasadena, CA (US); Alexander Kane, Santa Cruz, CA (US); Brett Goldsmith, San Diego, CA (US); Regis Paytavi, Costa Mesa, CA (US)

(73) Assignee: AMMR JOINT VENTURE, San Diego, CA (US)

( * ) Notice: Subject to any disclaimer, the term of this patent is extended or adjusted under 35 U.S.C. 154(b) by 207 days.

(21) Appl. No.: 16/912,501

(22) Filed: Jun. 25, 2020

(65) Prior Publication Data

US 2020/0326300 A1    Oct. 15, 2020

Related U.S. Application Data

(63) Continuation-in-part of application No. 16/459,298, filed on Jul. 1, 2019, now abandoned.

(60) Provisional application No. 62/866,312, filed on Jun. 25, 2019, provisional application No. 63/036,772, filed on Jun. 9, 2020, provisional application No. 62/692,520, filed on Jun. 29, 2018.

(51) Int. Cl.
| | | |
|---|---|---|
| *C12Q 1/44* | (2006.01) | |
| *G01N 27/414* | (2006.01) | |
| *C12Q 1/6897* | (2018.01) | |

(52) U.S. Cl.
CPC ........... *G01N 27/4145* (2013.01); *C12Q 1/44* (2013.01); *C12Q 1/6897* (2013.01)

(58) Field of Classification Search
CPC ....... C12Q 1/6897; C12Q 1/44; C12Q 1/6825
See application file for complete search history.

(56) References Cited

U.S. PATENT DOCUMENTS

| | | |
|---|---|---|
| 8,445,945 B2 | 5/2013 | Rothberg et al. |
| 9,339,790 B2 | 5/2016 | Vittadello et al. |
| 9,618,474 B2 | 4/2017 | van Rooyen et al. |
| 9,618,476 B2 | 4/2017 | Goldsmith |
| 9,857,328 B2 | 1/2018 | Hoffman |
| 9,859,394 B2 | 1/2018 | Hoffman et al. |
| 10,006,910 B2 | 6/2018 | Hoffman |
| 10,020,300 B2 | 7/2018 | Hoffman |
| 10,395,928 B2 | 8/2019 | Pan et al. |
| 10,429,381 B2 | 10/2019 | Hoffman |
| 10,494,670 B2 | 12/2019 | van Rooyen et al. |
| 10,607,989 B2 | 3/2020 | Hoffman |
| 2004/0238379 A1 | 12/2004 | Lindsay et al. |
| 2006/0223170 A1 | 10/2006 | Kamahori et al. |
| 2010/0133510 A1 | 6/2010 | Kim et al. |
| 2010/0233031 A1 | 9/2010 | Masters |
| 2010/0248209 A1 | 9/2010 | Datta et al. |
| 2010/0255984 A1 | 10/2010 | Sutter et al. |
| 2010/0279426 A1 | 11/2010 | Tour et al. |
| 2010/0327847 A1 | 12/2010 | Leiber et al. |
| 2011/0159481 A1 | 6/2011 | Liu et al. |
| 2011/0165557 A1 | 7/2011 | Ah et al. |
| 2011/0217763 A1 | 9/2011 | Rasooly et al. |
| 2011/0220805 A1 | 9/2011 | Gordon et al. |
| 2012/0214172 A1 | 8/2012 | Chen et al. |
| 2012/0220053 A1 | 8/2012 | Lee et al. |
| 2013/0034880 A1 | 2/2013 | Oldham |
| 2013/0089932 A1 | 4/2013 | Wu et al. |
| 2013/0204107 A1 | 8/2013 | Lee et al. |
| 2013/0270521 A1 | 10/2013 | Peng et al. |
| 2014/0042390 A1 | 2/2014 | Gruner et al. |
| 2014/0162390 A1 | 6/2014 | Afzali-Ardakani et al. |
| 2014/0312879 A1 | 10/2014 | Torsi et al. |
| 2015/0038378 A1 | 2/2015 | Cheng et al. |
| 2015/0218094 A1 | 8/2015 | Braunschweig et al. |
| 2015/0225783 A1 | 8/2015 | Mears et al. |

(Continued)

FOREIGN PATENT DOCUMENTS

| | | |
|---|---|---|
| CN | 101405410 A | 4/2009 |
| CN | 101466848 A | 6/2009 |

(Continued)

OTHER PUBLICATIONS

X. Fang et al., Highly Efficient Exosome Isolation and Protein Analysis by an Integrated Nanomaterial-Based Platform, Analytical Chemistry, American Chemical Society, Jan. 30, 2018, pp. 2787-2795.

(Continued)

*Primary Examiner* — Tekchand Saidha
(74) *Attorney, Agent, or Firm* — Kunzler Bean & Adamson; Tom Briscoe

(57) ABSTRACT

Apparatuses, systems, and methods are disclosed for target detection based on collateral cleavage of a reporter by an enzyme. A biologically gated transistor may include a channel and a reporter moiety immobilized to the channel. The state of the reporter moiety may affect one or more output signals from the biologically gated transistor when excitation conditions are applied to the biologically gated transistor and a sample fluid is applied in contact with the channel. A sample fluid may include an enzyme configured to activate in response to a target nucleic acid to cleave the reporter moiety. Excitation circuitry may apply the excitation conditions, and measurement circuitry may measure output signals from the biologically gated transistor. An analysis module may determine a parameter relating to presence of the target nucleic acid, based on the one or more measurements.

21 Claims, 10 Drawing Sheets

(56) References Cited

U.S. PATENT DOCUMENTS

| | | |
|---|---|---|
| 2015/0276709 A1 | 10/2015 | OHalloran et al. |
| 2015/0316523 A1 | 11/2015 | Patolsky et al. |
| 2016/0123919 A1 | 5/2016 | Johnson et al. |
| 2016/0290955 A1 | 10/2016 | Zhong et al. |
| 2017/0247754 A1 | 8/2017 | Edwards et al. |
| 2017/0299602 A1 | 10/2017 | Johnson, Jr. et al. |
| 2017/0365477 A1 | 12/2017 | Pan et al. |
| 2017/0365562 A1 | 12/2017 | Pan et al. |
| 2018/0037952 A1 | 2/2018 | Goldsmith |
| 2018/0245150 A1 | 8/2018 | Esfandyarpour et al. |
| 2018/0313782 A1 | 11/2018 | Rothberg et al. |
| 2018/0334708 A1 | 11/2018 | Rothberg et al. |
| 2019/0112643 A1 | 4/2019 | Aran et al. |
| 2019/0137443 A1 | 5/2019 | Balijepalli et al. |
| 2019/0181273 A1 | 6/2019 | van Rooyen et al. |
| 2019/0351665 A1 | 11/2019 | Lerner et al. |
| 2020/0181695 A1 | 6/2020 | van Rooyen et al. |
| 2021/0382045 A1 | 12/2021 | Aran et al. |

FOREIGN PATENT DOCUMENTS

| | | |
|---|---|---|
| CN | 101713772 A | 5/2010 |
| CN | 103076379 A | 5/2013 |
| JP | 2010513869 A | 4/2010 |
| WO | 2011045436 A1 | 4/2011 |
| WO | 2012050646 A3 | 4/2012 |
| WO | 2012112746 A1 | 8/2012 |
| WO | 2013033359 A1 | 3/2013 |

OTHER PUBLICATIONS

Ms. Chiriaco et al., "Lab-on-Chip for Exosomes and Microvesicles Detection and Characterization", MDPI Journal Sensors, Sep. 20, 2018, pp. 1-41.

D. Li et al., "When biomolecules meet graphene: from molecular level interactions to material design and applications", Royal Society of Chemistry, Nanoscale, Nov. 8, 2016, pp. 19491-19509.

L. Locascio et al., "Calculating Dissociation Rates of Tight Binders Using Kobs", Nanomedical Diagnostics Technical Note, Mar. 2018, pp. 1-3.

S. Afsahi et al., "Reproducible Characterization of GPCR and Small Molecule Compound Interactions Using Agile R100", Nanomedical Diagnostics Application Note, Dec. 2017, pp. 1-6.

"Solvent Correction versus In-line Reference Measurement", Nanomedical Diagnostics Technical Note, Nov. 2016, pp. 1-5.

DKH. Tsang et al., "Chemically Functionalised Graphene FET Biosensor for the Label-free Sensing of Exosomes", Scientific Reports, Sep. 26, 2019, pp. 1-10.

F. Wai et al., "Detection of exosomal biomarker by electric field-induced release and measurement (EFIRM)", Biosens Bioelectron, NIH Public Access, Jun. 15, 2013, pp. 1-13.

Nguyen et al. "Graphene Interfaced with Biological Cells: Opportunities and Challenges," The 5 Journal of Physical.

Mohanty et al. "Graphene-Based Single-Bacterium Resolution Biodevice and DNA Transistor: Interfacing Graphene Derivatives with Nanoscale and Microscale Biocomponents" Nano Lett., Nov. 5, 2008, vol. 8, No. 12, pp. 4469-4476.

X. Osteikoetxea et al., "Differential detergent sensitivity of extracellular vesicle subpopulations", Royal Society of Chemistry, Organic & Biomoecular Chemistry, Aug. 2015, pp. 1-9.

Y. Yu et al., "Electrical and Label-Free Quantification of Exosomes with a Reduced Graphene Oxide Field Effect Transistor Biosensor", Analytical Chemistry, American Chemical Society, Jul. 23, 2019, pp. 10679-10686.

W. Swaminathan et al., "Enhanced sub-micron colloidal particle separation with interdigitated microelectrode arrays using mixed AC/DC dielectrophoretic scheme", Biomed Microdevices, Apr. 2015, pp. 1-10.

S. Li et al., "CRISPR-Cas 12a-assisted nucleic acid detection", Cell Discovery vol. 4 No. 1, Apr. 24, 2018, pp. 1-4.

"Extended European Search Report", 20831413.8 European Patent Office, Jul. 18, 2022, pp. 1-52.

V. Pachauri et al. "Biologically Sensitive Field-Effect Transistors: from ISFETs to NanoFETs", Biochemical Society, Jun. 30, 2016, pp. 81-91.

Y. Li et al. , CRISPR/Cas Systems Towards Next-Generation Biosensing, CELPRESS Trends in Biotechnology, Dec. 2018, p. 1-14.

R. Haijan et al., "Detection of Unamplified Target Genes via GRISPR-Cas9 Immobilized on a Graphene Field-Effect Transistor", Nat Biomed Eng. Jun. 2019, pp. 1-24.

PCT/US2020/039678, Notification of Transmittal of the International Search Report and the Written Opinion of the International Search Authority, or the Declaration, Sep. 24, 2020.

ELECTRONIC DETECTION OF A TARGET BASED ON ENZYMATIC CLEAVAGE OF A REPORTER MOIETY

CROSS-REFERENCES TO RELATED APPLICATIONS

This application claims the benefit of U.S. Provisional Patent Application No. 62/866,312 entitled "Systems and Methods for Electronic Detection of Cleavage and Collateral Activity of CRISPR-associated Endonucleases" and filed on Jun. 25, 2019 for Kiana Aran et al.; claims the benefit of U.S. Provisional Patent Application No. 63/036,772 entitled "DYNAMIC EXCITATION AND MEASUREMENT OF BIOCHEMICAL INTERACTIONS" and filed on Jun. 9, 2020 for Kiana Aran et al.; and is a continuation-in-part application of and claims priority to U.S. patent application Ser. No. 16/459,298 entitled "Systems and Methods for Exosome Capture and Detection" and filed on Jul. 1, 2019 for Michael Heltzen et al., which claims the benefit of U.S. Provisional Patent Application No. 62/692,520 entitled "Exosome Capture and Sensing" and filed on Jun. 29, 2018 for Michael Heltzen et al.; each of which is incorporated herein by reference.

FIELD

The subject matter disclosed herein relates to biotechnology and more particularly relates to electronic detection of a target based on enzymatic cleavage of a reporter moiety.

BACKGROUND

Various biochemical assays exist for detecting a target molecule or moiety. Where the target is a nucleic acid, such as viral RNA sequence in a test to detect viral infection, or a cancer microRNA sequence in a test to detect cancer, some assays may involve amplifying the target using recombinase polymerase amplification (RPA), or another amplification technique. Operational requirements of a test system to detect a nucleic acid target and distinguish it from non-target sequences may be complex.

SUMMARY

Systems are disclosed for target detection based on collateral cleavage of a reporter by an enzyme. In one embodiment, a biologically gated transistor includes a channel and a reporter moiety immobilized to the channel. In some embodiments, a biologically gated transistor is configured such that one or more output signals from the biologically gated transistor are affected by a state of a reporter moiety in response to application of one or more excitation conditions to the biologically gated transistor and application of a sample fluid in contact with the channel. In a further embodiment, a sample fluid includes an enzyme configured to activate in response to a target nucleic acid to cleave the reporter moiety. In some embodiments, excitation circuitry is configured to apply the one or more excitation conditions to the biologically gated transistor. In further embodiments, measurement circuitry is configured to perform one or more measurements of at least one of the one or more output signals from the biologically gated transistor that are affected by the state of the reporter moiety. In some embodiments, an analysis module is configured to determine a parameter relating to presence of the target nucleic acid, based on the one or more measurements.

Apparatuses are disclosed for target detection based on collateral cleavage of a reporter by an enzyme. An apparatus, in one embodiment, includes a channel for a biologically gated transistor. In some embodiments, a reporter nucleic acid is immobilized to the channel. In some embodiments, a reporter nucleic acid immobilized to the channel causes one or more output signals from the biologically gated transistor to be affected by a state of the reporter nucleic acid in response to application of one or more excitation conditions to the biologically gated transistor and application of a sample fluid in contact with the channel. In further embodiments, a sample fluid includes a nuclease enzyme configured to activate in response to a target nucleic acid to cleave the reporter nucleic acid.

Methods are disclosed for target detection based on collateral cleavage of a reporter by an enzyme. A method, in one embodiment, includes providing a biologically gated transistor that includes a channel and a reporter moiety immobilized to the channel. In a further embodiment, a method includes applying a sample fluid to the channel, without applying a target amplification process to the sample fluid. In some embodiments, a method includes providing an enzyme within the sample fluid, where the enzyme is configured to activate in response to a target nucleic acid to cleave the reporter moiety. In some embodiments, a method includes applying one or more excitation conditions to the biologically gated transistor such that one or more output signals from the biologically gated transistor are affected by a state of the reporter moiety. In some embodiments, a method includes performing one or more measurements of at least one of the one or more output signals from the biologically gated transistor that are affected by the state of the reporter moiety. In some embodiments, a method includes determining a parameter relating to presence of the target nucleic acid, based on the one or more measurements.

An apparatus, in another embodiment, includes means for collaterally cleaving a reporter moiety in response to activation by a target nucleic acid. In a further embodiment, an apparatus includes means for detecting cleavage of the reporter moiety based on an interaction between the reporter moiety and a surface.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
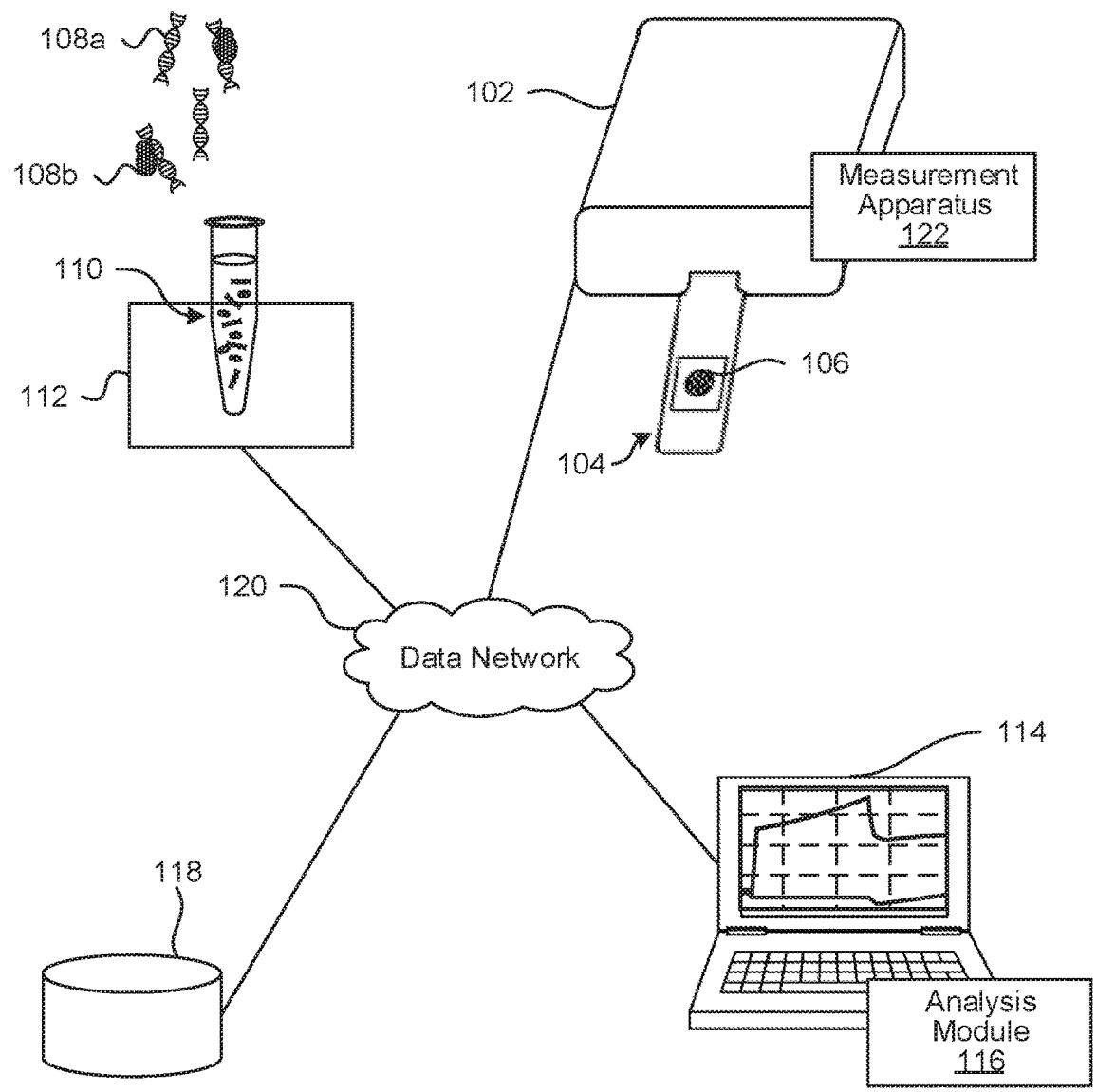
FIG. 1 is a perspective view illustrating one embodiment of a system for target detection based on collateral cleavage of a reporter by an enzyme.

As will be appreciated by one skilled in the art, aspects of the disclosure may be embodied as a system, method, or program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, embodiments may take the form of a program product embodied in one or more computer readable storage devices storing machine readable code, computer readable code, and/or program code, referred hereafter as code. The storage devices may be tangible, non-transitory, and/or non-transmission. The storage devices may not embody signals. In a certain embodiment, the storage devices only employ signals for accessing code.

Certain of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in code and/or software for execution by various types of processors. An identified module of code may, for instance, comprise one or more physical or logical blocks of executable code which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different computer readable storage devices. Where a module or portions of a module are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for embodiments may be written in any combination of one or more programming languages including an object oriented programming language such as Python, Ruby, Java, Smalltalk, C++, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A component, as used herein, comprises a tangible, physical, non-transitory device. For example, a component may be implemented as a hardware logic circuit comprising custom VLSI circuits, gate arrays, or other integrated circuits; off-the-shelf semiconductors such as logic chips, transistors, or other discrete devices; and/or other mechanical or electrical devices. A component may also be implemented in programmable hardware devices such as field programmable gate arrays, programmable array logic, programmable logic devices, or the like. A component may comprise one or more silicon integrated circuit devices (e.g., chips, die, die planes, packages) or other discrete electrical devices, in electrical communication with one or more other components through electrical lines of a printed circuit board (PCB) or the like. Each of the modules described herein, in certain embodiments, may alternatively be embodied by or implemented as a component.

A circuit, or circuitry, as used herein, comprises a set of one or more electrical and/or electronic components providing one or more pathways for electrical current. In certain embodiments, circuitry may include a return pathway for electrical current, so that a circuit is a closed loop. In another embodiment, however, a set of components that does not include a return pathway for electrical current may be referred to as a circuit or as circuitry (e.g., an open loop). For example, an integrated circuit may be referred to as a circuit or as circuitry regardless of whether the integrated circuit is coupled to ground (as a return pathway for electrical current) or not. In various embodiments, circuitry may include an integrated circuit, a portion of an integrated circuit, a set of integrated circuits, a set of non-integrated electrical and/or electrical components with or without integrated circuit devices, or the like. In one embodiment, a circuit may include custom VLSI circuits, gate arrays, logic circuits, or other integrated circuits; off-the-shelf semiconductors such as logic chips, transistors, or other discrete devices; and/or other mechanical or electrical devices. A circuit may also be implemented as a synthesized circuit in a programmable hardware device such as field programmable gate array, programmable array logic, programmable logic device, or the like (e.g., as firmware, a netlist, or the like). A circuit may comprise one or more silicon integrated circuit devices (e.g., chips, die, die planes, packages) or other discrete electrical devices, in electrical communication with one or more other components through electrical lines of a printed circuit board (PCB) or the like. Each of the modules described herein, in certain embodiments, may be embodied by or implemented as a circuit.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and program products according to embodiments. It will be understood that each block of the schematic flowchart diagrams and/or schematic block diagrams, and combinations of blocks in the schematic flowchart diagrams and/or schematic block diagrams, can be implemented by code. This code may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, other programmable data processing apparatus, or other devices to cause a series of operational steps to be performed on the computer, other programmable apparatus or other devices to produce a computer implemented process such that the code which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods, and program products according to various embodiments. In this regard, each block in the schematic flowchart diagrams and/or schematic block diagrams may represent a module, segment, or portion of code, which comprises one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate embodiments of like elements.

As used herein, a list with a conjunction of "and/or" includes any single item in the list or a combination of items in the list. For example, a list of A, B and/or C includes only A, only B, only C, a combination of A and B, a combination of B and C, a combination of A and C or a combination of A, B and C. As used herein, a list using the terminology "one or more of" includes any single item in the list or a combination of items in the list. For example, one or more of A, B and C includes only A, only B, only C, a combination of A and B, a combination of B and C, a combination of A and C or a combination of A, B and C. As used herein, a list using the terminology "one of includes one and only one of any single item in the list. For example, "one of A, B and C" includes only A, only B or only C and excludes combinations of A, B and C. As used herein, "a member selected from the group consisting of A, B, and C," includes one and only one of A, B, or C, and excludes combinations of A, B, and C." As used herein, "a member selected from the group consisting of A, B, and C and combinations thereof" includes only A, only B, only C, a combination of A and B, a combination of B and C, a combination of A and C or a combination of A, B and C.

Definitions

The term "biologically gated transistor," as used herein, refers to a transistor where current between source and drain terminals, through at least one channel, is capable of being gated, modulated, or affected by events, occurrences, or interactions within a sample fluid in contact with a surface of the channel. For example, an interaction of ions, molecules, or moieties within the sample fluid, or an interaction between the channel surface and ions, molecules, or moieties within the sample fluid, may be capable of gating, modulating, or effecting the channel current. The term "biologically gated transistor" may be used to refer to such a device in use, with a sample fluid applied to the surface of the channel, or to the same device before the sample fluid has been applied. The term "biologically gated transistor" may be used without regard to whether molecules or moieties within the sample fluid are biologically produced. For example, a biologically gated transistor may be gated by interactions between a biologically produced enzyme in the sample fluid and the enzyme's substrate, or may be gated by non-biological interactions within the sample fluid, but may still be referred to as "biologically gated."

The term "output signal," as used herein, refers to a measurable or detectable electrical signal from a biologically gated transistor, or to a result that can be calculated based on the measurable or detectable signal. For example, an output signal may be a voltage at one or more terminals of a biologically gated transistor, a current at one or more biologically gated transistors, a capacitance, inductance, or resistance (calculated based on applied and measured voltages and currents), a complex-valued impedance, a complex impedance spectrum, an electrochemical impedance spectrum, a threshold voltage, a Dirac voltage, a power spectral density, one or more network parameters (such as S-parameters or h-parameters), or the like.

The term "excitation condition," as used herein, refers to a physical, electrical, or chemical condition applied to a biologically gated transistor or to a sample for measurement by a biologically gated transistor. Excitation conditions may affect a state of a reporter moiety, which in turn may affect one or more output signals from the biologically gated transistor. For example, excitation conditions may include voltages, currents, frequencies, amplitudes, phases, or waveforms of electrical signals applied to a biologically gated transistor, one or more temperatures, one or more fluid flow rates, one or more wavelengths of electromagnetic radiation, or the like.

The term "nucleic acid," as used herein, refers to any form of RNA and/or DNA. For example, a nucleic acid may be single-stranded RNA, double-stranded DNA, single-stranded DNA (ssDNA), viral RNA, messenger RNA (mRNA), non-coding RNA (ncRNA), microRNA (miRNA), or the like. The term "nucleic acid" may be used to refer to a molecule of DNA or RNA, or to one or more polynucleotide or oligonucleotide strands as a part of a larger structure. For example, DNA may be chemically linked to another molecule or moiety, but may still be referred to as a nucleic acid despite not being an independent molecule of DNA. Similarly, a set of one or more DNA subsequences (contiguous or non-contiguous) within a longer DNA sequence may be referred to as a nucleic acid.

The term "moiety," as used herein, refers to a part of a molecule. For example, a moiety may be a nucleic acid portion of another molecule, a monosaccharide within a disaccharide, a mono- or disaccharide within a polysaccharide, an active part of a drug molecule, an inactive part of a drug molecule, a part of an enzyme molecule that binds to the enzyme's substrate, a part of the substrate molecule that binds to the enzyme, another part of an enzyme or substrate, or the like. In the singular form, the term "moiety" may be used to refer to a part of one molecule or to multiple instances of the same (or similar) type or moiety. For example, multiple strands of a nucleic acid, chemically bonded to a substrate, may be referred to as a nucleic acid moiety immobilized to the substrate. In the plural form, the term "moieties" may be used to refer to multiple types of moiety (e.g., an enzyme moiety and a substrate moiety) or to the same type of moiety for multiple molecules (e.g., a moiety of a protein for multiple molecules of that protein).

The term "enzyme," as used herein, refers to a protein, or a complex involving a protein, that acts on a substrate. For example, with reference to a CRISPR-associated (Cas)9 enzyme, guided by guide RNA to bind to and cleave a DNA substrate, the term "enzyme" may be used to refer to the Cas9 protein itself or to the complex of the protein with its associated guide RNA. The plural form "enzymes" may be used to refer to different types of enzyme, or to multiple instances of the same type of enzyme. The singular form "enzyme" may refer to one or more instances of a single type of enzyme. For example, adding multiple copies of the same Cas14 enzyme to a sample fluid may be described herein as adding an enzyme to the sample fluid.

The terms "cleave" and "cleavage," as used herein, refer to breakage of covalent bonds within a moiety to produce one or more fragments of the moiety. For example, cleavage of a nucleic acid moiety from the end of a strand may involve removing nucleotides one at a time from the end of the strand, so that the resulting fragments are removed nucleotides and the remainder of the strand. Similarly, cleavage of a nucleic acid moiety within a strand may produce two shorter strands as fragments. Cleavage of double-stranded DNA may include breaking bonds in both strands to produce separate fragments. As a further example, cleavage of a disaccharide or polysaccharide may produce shorter mono-, di-, or polysaccharides as fragments. Similarly, a monosaccharide may be cleaved to form smaller sugars or carbon chains as fragments (such as when glucose is cleaved to form pyruvate).

The terms "nuclease" and "nuclease enzyme," as used herein, refer to an enzyme capable of cleaving a nucleic acid. A nuclease may be an exonuclease that cleaves nucleic acids from the end, or an endonuclease that cleaves nucleic acid strands at sites within the strands. A nuclease may be a DNase that cleaves DNA, an RNase that cleaves RNA, a restriction enzyme that cleaves DNA or RNA at a cleavage site at or near a recognition site, or the like. A nuclease, in some embodiments, may be a Cas9, Cas12, Cas13, or Cas14 enzyme, a zinc-finger nuclease, a transcription activator-like effector nuclease (TALEN), or the like.

The term "target" refers to a molecule or moiety for which the presence, absence, concentration, activity, or other parameters relating to the target may be determined in an assay or test. For example, an assay using a biologically gated transistor may be used to determine the presence, absence, or concentration of a target. Compound terms such as "target nucleic acid," or "target moiety" may similarly be used to refer to a nucleic acid or moiety as the target of an assay. For enzyme-based tests as described herein, the term "target" may refer to a molecule or moiety that binds to or otherwise interacts with (or is acted upon by) an enzyme to activate further activity of the enzyme (such as cleavage of the target or cleavage of another non-target molecule or moiety)

The term "reporter," as used herein, refers to a molecule or moiety that may be cleaved, bound to, or otherwise modified by an enzyme in response to the enzyme being activated by the enzyme's interaction with its target. For a cis-acting enzyme, the reporter may be the target, or the reporter and the target may both be part of the same molecule. For a trans-acting enzyme, the reporter and the target may be separate molecules, or moieties of separate molecules. Compound terms such as "reporter nucleic acid," or "reporter moiety" may similarly be used to refer to a nucleic acid or moiety as a reporter.

The term "collateral cleavage," as used herein, refers to enzymatic cleavage of a reporter other than the target (e.g., by a trans-acting enzyme). For example, certain enzymes may be activated by a target including a particular sequence of nucleotides, to collaterally or indiscriminately cleave reporters without regard to whether the reporters include the target sequence.

Various biochemical methods for detecting a target molecule or moiety may be expensive or complex. For example, amplification of a target nucleic acid using recombinase polymerase amplification (RPA), or another amplification technique may be time-consuming, adding to the expense or complexity of a test to detect the target. Also, tests to detect amplified targets may be capable of detecting the presence or absence of the target, but not the pre-amplification level or concentration of the target. Optical techniques for target detection (e.g., by causing or quenching fluorescence in the presence of the target) may involve expensive optical components. Additionally, test equipment that is specifically configured for detection of one target may be unsuitable for detection of other targets.

By contrast, assays using biologically gated transistors, as disclosed herein, may provide low cost and low complexity for electronic target detection or characterization, with or without amplification of the target. Sensors including biologically gated transistors may be built using traditional electronics manufacturing techniques, leading to lower costs. Systems using biologically gated transistors may be capable of performing electronic target detection for a wide variety of targets, leading to lower overall cost for individual assays.

FIG. 1 is a schematic block diagram illustrating one embodiment of a system 100 for target detection based on collateral cleavage of a reporter by an enzyme. The system 100, in the depicted embodiment, includes one or more chip-based biosensors 104, a chip reader device 102, a sample prep apparatus 112, a computing device 114, a remote data repository 118, and a data network 120.

A chip-based biosensor 104, in the depicted embodiment, includes one or more biologically gated transistors 106, which are described in further detail below. In various embodiments, a chip-based biosensor 104 is a device including one or more solid two-dimensional sensor elements (such as biologically gated transistors 106 and/or other sensor elements) arranged on a solid support. The sensor elements may respond directly or indirectly to the presence of a proximate biochemical or biomolecular analyte or interaction, or both, in a sample on or sufficiently proximate to the sensor elements to produce an electrical or electromagnetic response signal suitable for amplification, filtering, digitization, and other analog and digital signal processing operations. A reporter moiety may be immobilized to a sensing surface such as the channel of a biologically gated transistor.

In some embodiments, a chip-based biosensor 104 may include a plurality of transistors where at least one of the transistors is a biologically gated transistor 106. In some embodiments, a chip-based biosensor 104 may include one or more additional sensors alongside biologically gated transistors 106. For example, various types of sensors may be included that use terahertz spectroscopy, surface-enhanced spectroscopy, quartz crystal microbalance, grating-coupled interferometry, and so forth. In some embodiments, a chip-based biosensor 104 may include further components such as a flow cell or fluid propulsion mechanism.

In the depicted embodiment, the chip reader device 102 includes circuitry for communicating with (e.g., sending electrical signals to or receiving electrical signals from) components of the chip-based biosensor 104. For example, a chip-based biosensor 104 may include a chip or integrated circuit with one or more biologically gated transistors 106, mounted to a printed circuit board with electrical contacts at one edge. A socket in the chip reader device 102 may include matching contacts, so that the chip-based biosensor 104 can be plugged into or removed from the chip reader device 102. Various other or further types of connectors may be used to provide a detachable coupling between a chip-based biosensor 104 and a chip reader device 102.

In a further embodiment, the chip reader device 102 may include circuitry for communicating via the data network 120. For example, the chip reader device 102 may communicate information about measurements performed using the chip-based biosensor 104 to the computing device 114 and/or to a remote data repository 118, over the data network. The data network 120, in various embodiments, may be the Internet, or may be another network such as a wide area network, metropolitan area network, local area network, virtual private network, or the like. In another embodiment, the chip reader device 102 may communicate information in another way, in addition to or in place of communicating over a data network 120. For example, the chip reader device 102 may display or print information, save information to a removable data storage device, or the like.

In the depicted embodiment, a measurement apparatus 122 is implemented by the chip-based biosensor 104 and/or the chip reader device 102. In various embodiments, a measurement apparatus 122 may include excitation circuitry to apply excitation conditions to a biologically gated transistor 106. Output signals from the biologically gated transistor 106 (such as electrical currents, voltages, capacitances, impedances, or the like) may be affected by the state of a reporter moiety immobilized to the channel of the biologically gated transistor 106, in response to the excitation conditions and the application of a sample fluid 110 in contact with the channel. For example, if the sample fluid contains an enzyme that activates in response to a target to cleave the reporter moiety, then the cleaved or uncleaved state of the reporter moiety (corresponding to the presence or absence of the target in the sample fluid 110) may affect one or more of the output signals. The measurement apparatus 122 may include measurement circuitry to perform one or more measurements of at least one of the output signals that are affected by the state of the reporter moiety. Various embodiments of a measurement apparatus 122 are described in further detail below.

In various embodiments, target detection by a system 100 may be based on the interaction between a reporter moiety and a surface. For example, in one embodiment, a reporter moiety may be immobilized to the channel of a biologically gated transistor 106, so that the interaction between the reporter moiety and the surface is that the reporter moiety either remains on the channel surface or has fragments cleaved away from the channel surface depending on whether the reporter is cleaved, thus affecting an electric potential at the surface and a corresponding output signal of the biologically gated transistor 106. In another embodiment, a reporter moiety may be provided within the sample fluid 110 applied to a biologically gated transistor 106, and the interaction between the reporter moiety and the surface may be that larger particles of the uncleaved reporter or cleaved fragments of the reporter adsorb to the channel surface depending on whether the reporter is cleaved or uncleaved, similarly affecting the electric potential at the channel surface.

Additionally, although the system 100 includes a biologically gated transistor 106 in the depicted embodiment, a system in another embodiment may include other or further means for detecting cleavage of a reporter moiety based on an interaction between the reporter moiety and a surface. For example a surface such as a metal film, a graphite surface, or a piece of graphene, may be used as a working electrode in an electrochemical system that includes a reference electrode to measure an electrochemical potential and a counter electrode to modify an electrochemical potential. Interaction between the reporter moiety and the surface of the working electrode may include removal of fragments of the reporter from the surface or adsorption of fragments to the surface as described above for the biologically gated transistor 106, if cleavage of the reporter occurs, thus affecting an output signal such as an electrochemical impedance spectrum between the working electrode and the sample fluid 110. This may be similar or equivalent to using a biologically gated transistor 106 and measuring the channel capacitance (between the channel and the sample fluid) rather than the channel current. Some embodiments of a chip-based biosensor 104 may include a capacitive sensor in place of or in addition to a biologically gated transistor 106.

In some embodiments, a chip-based biosensor 104 may include the measurement apparatus 122. For example, excitation circuitry and/or measurement circuitry may be provided on the same chip as a biologically gated transistor 106, or on the same package, on the same printed circuit board, or the like, as part of a chip-based biosensor 104. In another embodiment, the chip reader device 102 may include the measurement apparatus 122. For example, excitation circuitry and/or measurement circuitry may be provided in a chip reader device 102 so that the excitation circuitry and/or measurement circuitry is reusable with multiple chip-based biosensors 104.

In another embodiment, a chip-based biosensor 104 and a chip reader device 102 may both include portions of a measurement apparatus 122. For example, the chip-based biosensor 104 may include portions of the excitation circuitry, such as a resistive heater for temperature control of the biologically gated transistor 106, and the chip reader device 102 may include other portions of the excitation circuitry such as a voltage or current source. In various embodiments, excitation circuitry, measurement circuitry and/or other components of a measurement apparatus 122 may be disposed between a chip-based biosensor 104 and a chip reader device 102 in various other or further ways.

Additionally, although the system 100 in the depicted embodiment includes a chip-based biosensor 104 that may be coupled to or removed from a chip reader device 102, the functions and/or components of a chip-based biosensor 104 and a chip reader device 102 may be integrated into a single device in another embodiment. Conversely, in some embodiments, a system may include multiple devices rather than a single chip reader device 102. For example, excitation circuitry and/or measurement circuitry for a measurement apparatus 122 may include lab bench hardware such as source measure units, function generators, bias tees, chemical impedance analyzers, lock-in amplifiers, data acquisition devices, or the like, which may be coupled to a chip-based biosensor 104.

The sample prep apparatus 112, in the depicted embodiment, is configured to automatically or semi-automatically prepare the sample fluid 110. In some embodiments, a sample prep apparatus 112 may include automated dispensing equipment such as a dispensing robot and/or a fluidic system. In some embodiments, a sample prep apparatus 112 may include its own controller and user interface for setting sample prep parameters such as incubation time and temperature for the sample fluid 110. In some embodiments, a sample prep apparatus 112 may be controlled via the data network 120. For example, the computing device 114 or the measurement apparatus 122 may control the sample prep apparatus 112.

In another embodiment, a system 100 may omit a sample prep apparatus 112, and a sample fluid 110 may be manually prepared. In some embodiments, preparing a sample fluid 110 may include obtaining or preparing a sample of a fluid in which a target may be observed (or the absence of a target may be detected). In some embodiments, preparing a sample fluid 110 may include adding an enzyme configured to activate in response to a target to cleave a reporter. In some embodiments, a sample fluid 110 once obtained may be applied directly to the chip-based biosensor 104. For example, in some embodiments, the chip-based biosensor 104 may be used to test for the presence of a target in blood, and the blood may be applied to the chip-based biosensor 104 as the sample fluid 110. In another embodiment, further sample prep steps to prepare a sample fluid 110 may include the addition of reagents, concentration or dilution, heating or cooling, centrifuging, or the like. Various other or further preparation techniques may be used to prepare a sample fluid 110 for use with a measurement apparatus 122.

The sample fluid 110, in various embodiments, may include one or more types of biomolecules 108. Biomolecules 108, in various embodiments, may be any molecules that are produced by a biological organism, including large polymeric molecules such as proteins, polysaccharides, lipids, and nucleic acids (DNA and RNA) as well as small molecules such as primary metabolites, secondary metabolites, and other natural products. For example, in the depicted embodiment, the sample fluid 110 includes target nucleic acids 108a and enzymes 108b that interact with the target nucleic acids 108a. Activation of enzymes 108b by targets 108a may be detected based on cleavage of reporters by the activated enzymes 108b. Parameters relating to the target 108a, such as the presence, absence 108a, or concentration of the target 108a may be determined using a chip-based biosensor 104, based on cleavage of the reporters.

The computing device 114, in the depicted embodiment, implements an analysis module 116. In various embodiments, a computing device 114 may be a laptop computer, a desktop computer, a smartphone, a handheld computing device, a tablet computing device, a virtual computer, an embedded computing device integrated into an instrument, or the like. In further embodiment, a computing device 114 may communicate with the measurement apparatus 122 via the data network 120. The analysis module 116, in certain embodiments, is configured to determine a parameter relating to presence of a target nucleic acid, based on one or more measurements of output signals from a biologically gated transistor 106, where the measurements are taken by the measurement apparatus 122. In various embodiments, an analysis module 116 may determine various parameters relating to the presence of a target nucleic acid, such as an indication of whether or not the target nucleic acid is present in the sample fluid, a concentration of the target nucleic acid or another parameter corresponding to or related to the concentration, an indication of whether or not (or to what extent) the reporter moiety was cleaved, a determination of the rate of cleavage, or the like.

In the depicted embodiment, the analysis module 116 is separate from the measurement apparatus 122, and is implemented by a computing device 114 separate from the measurement apparatus 122. In another embodiment, the analysis module 116 may be partially or fully integrated with the measurement apparatus 122. For example, the measurement apparatus 122 may include special-purpose logic hardware and/or a processor executing code stored in memory to implement all or part of the analysis module 116. In some embodiments, the analysis module 116 may be implemented as an embedded processor system or other integrated circuits that form part of a chip-based biosensor 104 and/or part of a chip reader device 102. In some embodiments, where an analysis module 116 is integrated with the measurement apparatus 122, a system 100 may omit a separate computing device 114.

The remote data repository 118, in various embodiments, may be a device or set of devices remote from the measurement apparatus 122 and capable of storing data. For example, the remote data repository 118 may be, or may include, a hard disk drive, a solid-state drive, a drive array, or the like. In some embodiments, the remote data repository 118 may be a data storage device within the computing device 114. In some embodiments, a remote data repository 118 may be network attached storage, a storage area network, or the like.

In some embodiments, the measurement apparatus 122 (e.g., a chip-based biosensor 104 and/or a chip reader device 102) may include communication circuitry that transmits measurement information to the remote data repository 118. Measurement information may be measurements from biologically gated transistors 106, or information about the measurements, such as calculated quantities based on the raw measurements. The analysis module 116 may communicate with the remote data repository 118 to determine one or more parameters relating to presence of a target nucleic acid based on the information stored by the remote data repository 118. In further embodiments, the analysis module 116 may store analysis results to the remote data repository 118. In another embodiment, however, the analysis module 116 may receive measurement information from the measurement apparatus 122 directly or over the data network 120, and a remote data repository 118 may be omitted (e.g., in favor of local data storage).

Figure 2:
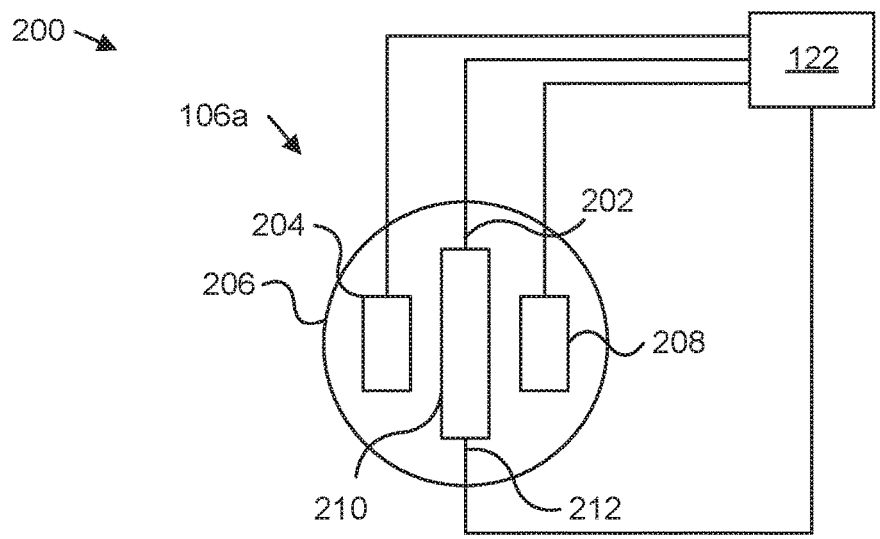
FIG. 2 is a schematic block diagram illustrating one embodiment of an apparatus for target detection based on collateral cleavage of a reporter by an enzyme, including one embodiment of a biologically gated transistor.

FIG. 2 is a schematic block diagram illustrating one embodiment of an apparatus 200 for target detection based on collateral cleavage of a reporter by an enzyme, including one embodiment of a biologically gated transistor 106a, coupled to a measurement apparatus 122. The biologically gated transistor 106a is depicted in a top view. The biologically gated transistor 106a and the measurement apparatus 122 in the depicted embodiment may be substantially as described above with reference to FIG. 1, and are described further below.

The biologically gated transistor 106a, in the depicted embodiment, includes a source 212, a drain 202, a channel 210, a reference electrode 208, a counter electrode 204, and a liquid well 206, which are described below. In general, in various embodiments, a biologically gated transistor 106a may include at least one channel 210 capable of conducting an electrical current between the source 212 and the drain 202. As in an insulated-gate field-effect transistor, current between the source 212 and the drain 202 depends not only not only on a voltage difference between the source 212 and the drain 202 but on certain conditions that affect the conductivity of the channel 210. However, an insulated-gate field-effect transistor is a solid-state device where a gate electrode is separated from the channel by a thin dielectric layer, so that the channel conductivity is modulated by the gate-to-body (or gate-to-source) voltage. Conversely, in various embodiments, channel conductivity (and a resulting drain-to-source current) for a biologically gated transistor 106a may be modulated, gated, or affected by liquid-state events. In particular, a sample fluid 110 may be applied to the biologically gated transistor 106a in contact with the channel 210, so that the channel conductivity depends on (or is gated or modulated by) a state of moieties within the sample fluid 110.

In various embodiments, the source 212, the drain 202, a channel 210, a reference electrode 208, and a counter electrode 204 may be formed on a substrate (not shown), such as an oxide or other dielectric layer of a silicon wafer or chip. Certain components of the biologically gated transistor 106a may be formed to be in contact with a sample fluid 110. For example, upper surfaces of the channel 210, the reference electrode 208 and the counter electrode 204 may be exposed or bare for direct interaction with the sample fluid 110. Other components may be covered or electrically insulated from the sample fluid 110. For example, the source 212 and drain 202 may be covered by an insulating layer such as silicon dioxide, silicon nitride, or another dielectric, so that current flows between the source 212 and drain 202 through the channel 210, without the sample fluid 110 creating a short circuit or an alternative or unintended current path between the source 212 and drain 202.

The liquid well 206 may be a structure to contain the sample fluid 110 in a region above the other components of the biologically gated transistor 106a. For example, the liquid well 206 may be a ridge of epoxy, a thermosetting resin, a thermoplastic, or the like. The liquid well 206 may be deposited on the substrate, formed as an opening in the chip packaging for the biologically gated transistor 106a, or the like.

The channel 210, in some embodiments, is made of a highly sensitive conducting material such as graphene. In further embodiments, a graphene channel 210 may be deposited on the substrate for the biologically gated transistor 106a by chemical vapor deposition (CVD). In some embodiments, the channel 210 may be made from another two-dimensional material which has strong in-plane covalent bonding and weak interlayer interactions. Such materials may be referred to as van der Waals materials. For example, in various embodiments, a channel 210 may be made from graphene nanoribbons (GNR), bilayer graphene, phosphorene, stanine, graphene oxide, reduced graphene, fluorographene, molybdenum disulfide, gold, silicon, germanene, topological insulators, or the like. Various materials that conduct and exhibit field-effect properties, and are stable at room temperature when directly exposed to various solutions, may be used in a biologically gated transistor 106a. Materials that may be suitable for forming a channel 210 of a biologically gated transistor 106a may include silicon surfaces, carbon electrodes, graphene, or two-dimensional materials other than graphene. Similar materials may also be used in electrochemical or capacitive sensors. In various implementations, using a biologically gated transistor 106a with one or more channels 210 formed from planar two-dimensional van der Waals materials improves manufacturability, and lowers costs compared with one-dimensional alternatives, such as carbon nanotubes.

The source 212 and drain 202 are disposed at opposite ends of the channel 210 so that a current conducted through the channel 210 is conducted from the drain 202 to the source 212, or from the source 212 to the drain 202. In various embodiments, the source 212 and drain 202 may be made of conductive material such as gold, platinum, polysilicon, or the like. In some embodiments, the source 212 may be coupled to the substrate of the biologically gated transistor 106a (e.g., the silicon below the oxide or other dielectric layer) so that a bias voltage (or another bias signal) applied to the source 212 also biases the substrate under the channel 210. In another embodiment, a biologically gated transistor 106a may include a separate body terminal (not shown) for biasing the substrate.

The terms "source" and "drain" may be used herein to refer to conductive regions or electrodes that directly contact the channel 210, or to leads, wires or other conductors connected to those regions or electrodes. Additionally, the terms "source" and "drain" are used as the conventional names for terminals of a transistor, but without necessarily implying a type of charge carrier. For example, a graphene channel 210 may conduct electricity with electrons or holes as the charge carriers depending on various external conditions (such as the excitation conditions applied by the measurement apparatus 122 and the cleaved or uncleaved state of a reporter moiety), and the charge carriers may flow from the source 212 to the drain 202, or from the drain 202 to the source 212.

In various embodiments, one or more output signals from the biologically gated transistor 106a may be affected by excitation conditions and by a state of a reporter moiety. As defined above, the excitation conditions may be physical, electrical, or chemical conditions applied to the biologically gated transistor 106a. Excitation conditions such as constant bias voltages (or signals), time-varying excitation voltages (or signals), temperature conditions, or the like may be applied to the biologically gated transistor 106a or to the sample fluid 110 by the measurement apparatus 122. The cleaved or uncleaved state of a reporter moiety may depend on whether (or to what extent) an enzyme was activated by a target, and thus may depend on the presence, absence, or concentration of the target. The interaction of the reporter moiety (or its fragments after cleavage) with the channel 210 may gate or modulate the channel conductivity, affecting one or more output signals. The output signals may be, or may include, a channel current, a voltage, a capacitance, inductance, or resistance (calculated based on applied and measured voltages and currents), a complex-valued impedance, a complex impedance spectrum, an electrochemical impedance spectrum, a Dirac voltage, a power spectral density, one or more network parameters (such as S-parameters or h-parameters), or the like.

In various embodiments, a layer that functions as a dielectric may form near the surface of a channel 210 for a biologically gated transistor, or near a similar surface for another sensor such as a capacitive or electrochemical sensor. One or more layers of ions may form near the channel surface when a fluid is applied in contact with the channel surface. For example, a double layer of ions may include a first layer of ions attracted or adsorbed to the channel surface and a second layer of ions attracted to the ions in the first layer. Or, if the channel has been functionalized by immobilizing certain molecules or moieties (e.g., proteins, peptides, surfactants, polymers such as polyethylene glycol, or the like) to the channel surface, forming an ion-permeable layer with a net charge, then ions from the fluid may diffuse into the ion-permeable layer of immobilized molecules or moieties due to the Gibbs-Donnan effect, forming a Donnan equilibrium region. In either case, charges near the channel surface may act as a dielectric between the channel 210 (or a similar surface in another type of sensor) and the bulk of the sample fluid 110. Cleavage of a reporter may result in the addition or removal of reporter fragments in this dielectric layer, or a change of state for the reporter within the dielectric layer, thus affecting an output signal such as a channel current or capacitance.

In some embodiments, the reporter moiety may be immobilized to the surface of the channel 210. Immobilizing a reporter moiety to the channel 210 may include chemically or physically linking the reporter to the channel. For example, where the reporter moiety includes polymeric strands of subunits chained together such as chains of nucleotides in DNA or RNA strands, chains of monosaccharides in polysaccharides, or the like, immobilizing the reporter to the channel 210 may include linking one or both ends of strands to the channel, or may include linking reporter molecules together in a hydrogel with the hydrogel backbone formed by strands of the reporter, and chemically linking or physically adhering the hydrogel to the channel. With a reporter immobilized to the channel 210, cleavage of the reporter results in fragments of the reporter diffusing into the sample fluid or being rinsed away in a rinse step, affecting the electric field near the channel 210, and thus affecting an output signal due to the field-effect sensitivity of the channel 210.

In another embodiment, however, a channel 210 may be bare or unfunctionalized graphene (or include another non-biological material such as a hydrogel or polymer), and a reporter molecule or moiety may be provided within the sample fluid 110. Where the reporter is provided in the sample fluid 110 instead of being immobilized to the channel 210, the reporter may be adsorbed to the channel, but cleavage of the reporter may result in fragments of the reporter rather than intact copies of the reporter being adsorbed to the channel. The difference between adsorption of the reporter and the reporter fragments may affect the electric field near the channel 210, thus affecting an output signal due to the field-effect sensitivity of the channel 210.

In another embodiment, a channel 210 may be bare or unfunctionalized, but magnetic or non-magnetic particles in the range of about 1 nm to 10 µm in diameter (which may be referred to as "beads") may be functionalized with reporter moieties as described above for a channel 210 and added to the sample fluid 110. Output signals from the biologically gated transistor 106a may be sensitive to the state of reporter moieties on the beads. With magnetic beads, a magnetic field may be applied to attract the beads towards the channel 210 out of the bulk solution of the sample fluid 110, so that the output signals are more strongly affected by the beads in proximity to the channel 210.

In various embodiments, a liquid (e.g., the sample fluid 110) applied to the channel 210 may be referred to as a liquid gate for the biologically gated transistor 106a, because one or more of the output signals for the biologically gated transistor 106a are affected by conditions, such as a state of the reporter moiety, within the liquid gate. In addition, in various embodiments, a biologically gated transistor 106a may include one or more gate electrodes for detecting and/or adjusting a voltage or electric potential of the liquid gate. For example, in the depicted embodiment, the biologically gated transistor 106a includes a reference electrode 208 for measuring an electrochemical potential of the sample fluid 110, and a counter electrode 204 for adjusting the electrochemical potential of the sample fluid 110.

In some embodiments, an electric potential may develop at the interface between the sample fluid 110 and the reference electrode 208 and/or the counter electrode 204. Thus, in some embodiments, a reference electrode 208 may be made of a material with a known or stable electrode potential. In another embodiment, however, a reference electrode 208 may be a pseudo-reference electrode that does not maintain a constant electrode potential. Nevertheless, measurements of the electrochemical potential of the sample fluid 110 via a pseudo-reference electrode may still be useful as output signals or as feedback for adjusting the electrochemical potential of the sample fluid 110 via the counter electrode 204. In some embodiments, the reference electrode 208 and/or the counter electrode 204 may be made of non-reactive materials such as gold or platinum.

In some embodiments, a biologically gated transistor 106a may be made using photolithography or other commercially available chip fabrication techniques. For example, a thermal oxide layer may be grown on a silicon substrate, and metal components such as a source 212, drain 202, reference electrode 208 and/or the counter electrode 204 may be deposited or patterned on the thermal oxide layer. A graphene channel 210 may be formed using chemical vapor deposition. The use of conventional fabrication techniques may provide low-cost biologically gated transistors 106a, especially in comparison to sensors using high-cost materials such as carbon nanotubes or specialty fabrication techniques. Various other or further configurations of biologically gated transistors 106a and ways to fabricate biologically gated transistors 106a are discussed in U.S. patent application Ser. No. 15/623,279 entitled "PATTERNING GRAPHENE WITH A HARD MASK COATING"; U.S. patent application Ser. No. 15/623,295 entitled "PROVIDING A TEMPORARY PROTECTIVE LAYER ON A GRAPHENE SHEET"; U.S. patent application Ser. No. 16/522,566 entitled "SYSTEMS FOR TRANSFERRING GRAPHENE"; and U.S. Pat. No. 10,395,928 entitled "DEPOSITING A PASSIVATION LAYER ON A GRAPHENE SHEET"; each of which is incorporated herein by reference.

Figure 3:
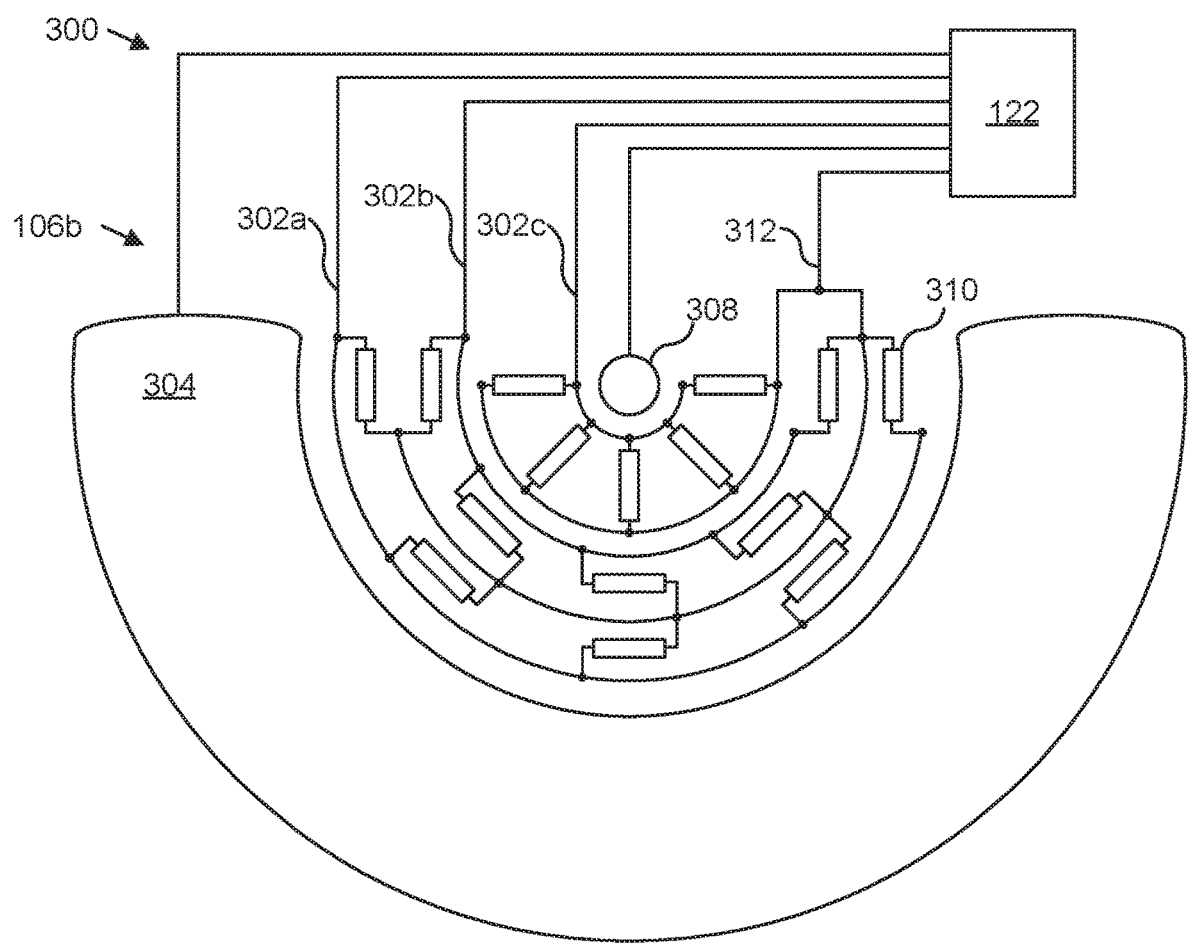
FIG. 3 is a schematic block diagram illustrating another embodiment of an apparatus for target detection based on collateral cleavage of a reporter by an enzyme, including another embodiment of a biologically gated transistor.

FIG. 3 is a schematic block diagram illustrating another embodiment of an apparatus 300 for target detection based on collateral cleavage of a reporter by an enzyme, including another embodiment of a biologically gated transistor 106b, coupled to a measurement apparatus 122. As in FIG. 2, the biologically gated transistor 106b is depicted in a top view. The biologically gated transistor 106b and the measurement apparatus 122 in the depicted embodiment may be substantially as described above with reference to FIGS. 1 and 2, and are described further below.

In the depicted embodiment, the biologically gated transistor 106b includes a source 312, a plurality of drains 302, a plurality of channels 210, a reference electrode 308, and a counter electrode 304, which may be substantially similar to the source 212, drain 202, channel 210, reference electrode 208, and counter electrode 204 described above with reference to FIG. 2. (A liquid well similar to the liquid well 206 of FIG. 2 is not depicted in FIG. 3 but may similarly be provided as part of the biologically gated transistor 106b)

However, in the depicted embodiment, the biologically gated transistor 106b includes a plurality of channels 310, and a plurality of drains 302. In various embodiments, a plurality of channels 310 may be homogeneous or heterogeneous. For example, homogeneous channels 310 may be bare or unfunctionalized graphene, or may have reporter moieties immobilized to the channels in the same way. Conversely, heterogeneous channels 310 may be a mixture of bare and functionalized graphene channels 310, a mixture of channels 310 that are functionalized in more than one way (optionally including one or more unfunctionalized channels 310) or the like. For example, heterogeneous channels 310 may include a subset of channels 310 with reporter moieties immobilized to the channels, and another subset of channels without reporter moieties, for tests other than target detection. In some embodiments, providing a plurality of heterogeneous channels 310 may make a biologically gated transistor 106b useful for a variety of different tests that rely on events near the surfaces of the channels 310. Additionally, the use of multiple channels 310 may provide redundancy to mitigate damage to any individual channel 310 (e.g., mechanical damage from a pipette tip used to apply the sample fluid 110), and may make the biologically gated transistor 106b sensitive to biochemical interactions in the sample fluid 110 across a greater surface area than in a single-channel device.

In some embodiments, a biologically gated transistor 106b may include a plurality of drains 302 coupled to the channels 310. In some embodiments, one drain 302 may be provided per channel 310 so that each channel 310 can be independently biased. In some embodiments, however, channels 310 may be coupled to drains 302 in groups, so that the channels 310 of a group can be biased together in parallel, but different groups can be biased differently. For example, in the depicted embodiment, the biologically gated transistor 106b includes fifteen channels 310, coupled to three drains 302a-c, so that one of the drains 302 can be used to bias a group of five channels 310. In another embodiment, a plurality of channels 310 may be coupled in parallel to a single drain 302.

In the depicted embodiment, the channels 310 are coupled in parallel to one source 312. For some measurements, the source 312 may be coupled to ground (e.g., 0 volts, or another reference voltage). In another embodiment, however, channels 310 may be coupled to a plurality of sources 312, allowing different measurements to be made with different source biases. For example, channels 310 may be coupled to multiple sources 312 individually or in groups, as described above for the plurality of drains 302.

In the depicted embodiment, the reference electrode 308 and the counter electrode 304 are disposed so that the channels 310 are between the reference electrode 308 and the counter electrode 304. In this configuration, the electrochemical potential of the liquid gate may be modified via the counter electrode 304 and monitored via the reference electrode 308, so that the electrochemical potential near the channels 310 is close to the modified and/or monitored potential. Additionally, in the depicted embodiment, the counter electrode 304 is significantly larger than the channels 310 or the reference electrode 308, so that modifications to the electrochemical potential of the liquid gate made via the counter electrode 304 quickly occur across a large surface area, and in a large volume of the sample fluid 110.

Although FIGS. 2 and 3 depict individual biologically gated transistors 106a, 106b, a chip-based biosensor 104 in various embodiments may include a plurality of biologically gated transistors 106, which may be homogeneously or heterogeneously configured. For example, the homogeneous or heterogeneous configurations described above for multiple channels 310 in one biologically gated transistor 106b may similarly apply to multiple biologically gated transistors 106, each with their own independent source, drain, reference, and counter terminals.

Figure 4:
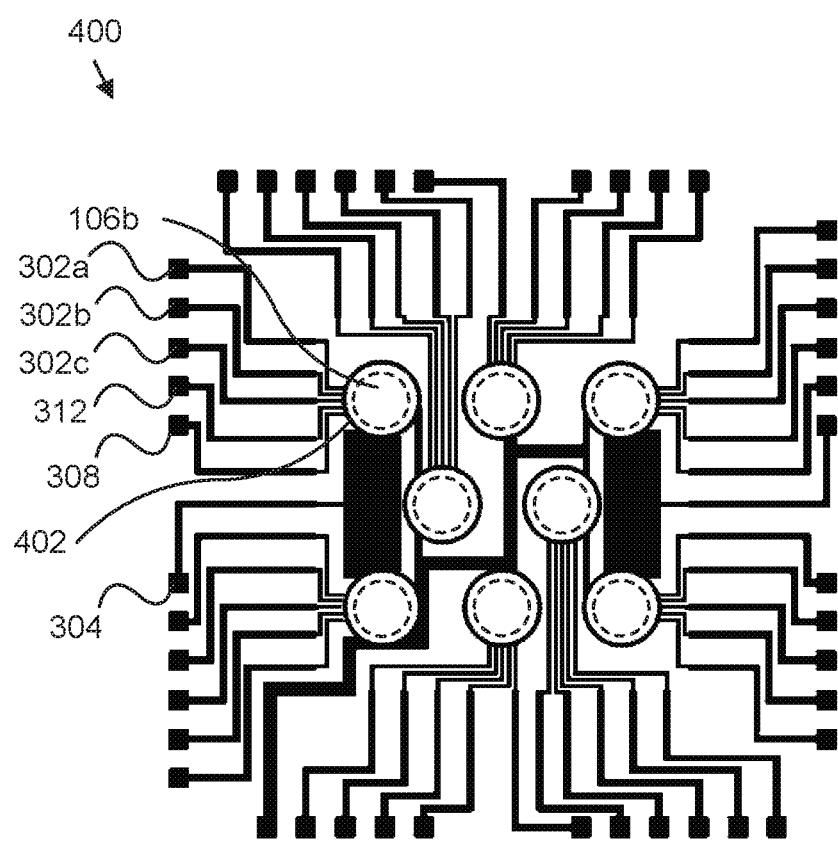
FIG. 4 is a top view illustrating one embodiment of an array of biologically gated transistors.
Figure 5:
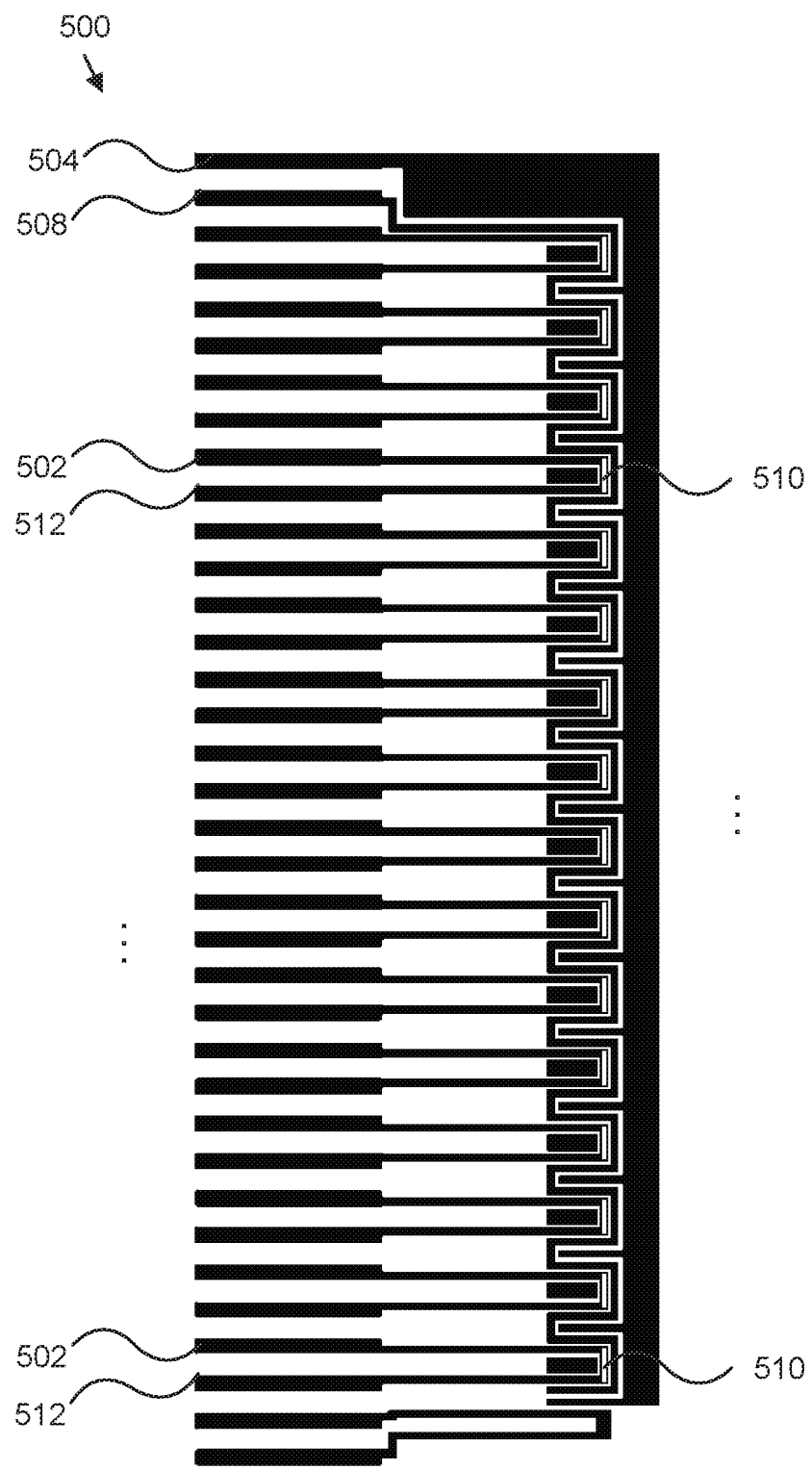
FIG. 5 is a top view illustrating another embodiment of an array of biologically gated transistors.

FIGS. 4 and 5 depict pluralities of biologically gated transistors 106, in two-dimensional or linear arrays (respectively). A system 100 or a chip-based biosensor 104 may include a plurality of biologically gated transistors 106 with reporter moieties immobilized to channels. The plurality of biologically gated transistors 106 in an array may include at least one biologically gated transistor with a reporter moiety immobilized to the channel, as described above with reference to FIGS. 1-3. A measurement apparatus 122 may include excitation circuitry to apply excitation conditions to the plurality of biologically gated transistors 106 in the array, and may include measurement circuitry to perform measurements for the plurality of biologically gated transistors 106 in the array. An analysis module 116 may determine parameters relating to the plurality of biologically gated transistors 106 in the array. For example, the analysis module 116 may determine whether cleavage of reporters occurred, a rate of cleavage, whether a target is present, a concentration of the target, or the like, for each of the transistors 106 in the array. In various embodiments, a multi-transistor array may be used to detect different targets at different transistors, to compare results from a sample fluid to results from a control fluid or the like.

FIG. 4 is a top view illustrating one embodiment of an array 400 of biologically gated transistors 106. In the depicted embodiment, the biologically gated transistors 106 are the biologically gated transistors 106b described above including three drains 302a-c, one source 312, and a reference electrode 308. In another embodiment, an array 400 may include another type or configuration of biologically gated transistor 106. Counter electrodes 304 in the depicted embodiment are provided to modify the electrical potential of the sample fluid 110.

In the depicted embodiment, a plurality of biologically gated transistors 106b (indicated by dashed circles) are disposed in a two-dimensional array of droplet locations 402 (indicated by solid circular outlines) on a substrate such as a chip for a chip-based biosensor 104. A liquid barrier or hydrophobic coating may be applied to the substrate in between the droplet locations. A liquid barrier or hydrophobic coating may be similar to the material described above with reference to FIG. 2 for forming a liquid well 206. In some embodiments, a two-dimensional array 400 of biologically gated transistors 106 may be used with multiple droplets deposited on the chip-based biosensor 104, or with flow channels perpendicular to the surface of the chip-based biosensor 104.

In the depicted embodiment, the droplet locations are in a triangular array, in which each droplet location is 4.5 mm away from its nearest neighbors. In another embodiments, the droplet locations may be in a square array, or may be arranged in another two-dimensional arrangement, and may be closer or further than 4.5 mm apart. In the depicted embodiment, the array 400 includes eight droplet locations. In another embodiment, an array 400 may include more or fewer droplet locations, such as two or four droplet locations, or several hundred to several thousand droplet locations.

FIG. 5 is a top view illustrating another embodiment of an array 500 of biologically gated transistors. In the depicted embodiment, the biologically gated transistors are disposed in a linear array of locations on a substrate such as a chip for a chip-based biosensor 104. Each transistor includes a channel 510 that links a drain 502 to a source 512, as described above. A reference electrode 508 and a counter electrode 504 run along the side of the array 500 in the depicted embodiment, to measure and/or modify the electrochemical potential within the sample fluid 110. In another embodiment, a plurality of reference electrodes 508 and/or counter electrodes 504 may be provided.

In some embodiments a linear array 500 of biologically gated transistors may be provided with a line of droplet locations separated by a liquid barrier or hydrophobic coating as described above with reference to FIG. 4, or may be provided without a liquid barrier or hydrophobic coating between channels 510. In some embodiments, a linear array 500 of biologically gated transistors 106 may be used with multiple droplets deposited on the chip-based biosensor 104 in a line, or with flow channels perpendicular to the surface of the chip-based biosensor 104. In some embodiments, however, a linear array 500 of biologically gated transistors 106 may be used with flow channels parallel to the surface of the chip-based biosensor 104, so that sample fluid travels over the transistors 106 of the array 500 in sequence. In comparison to the two-dimensional array 400 depicted in FIG. 4, the linear array 500 depicted in FIG. 5 may use more chip area on a chip-based biosensor, but may be less expensive overall due to simplified chip packaging and assembly.

Figure 6:
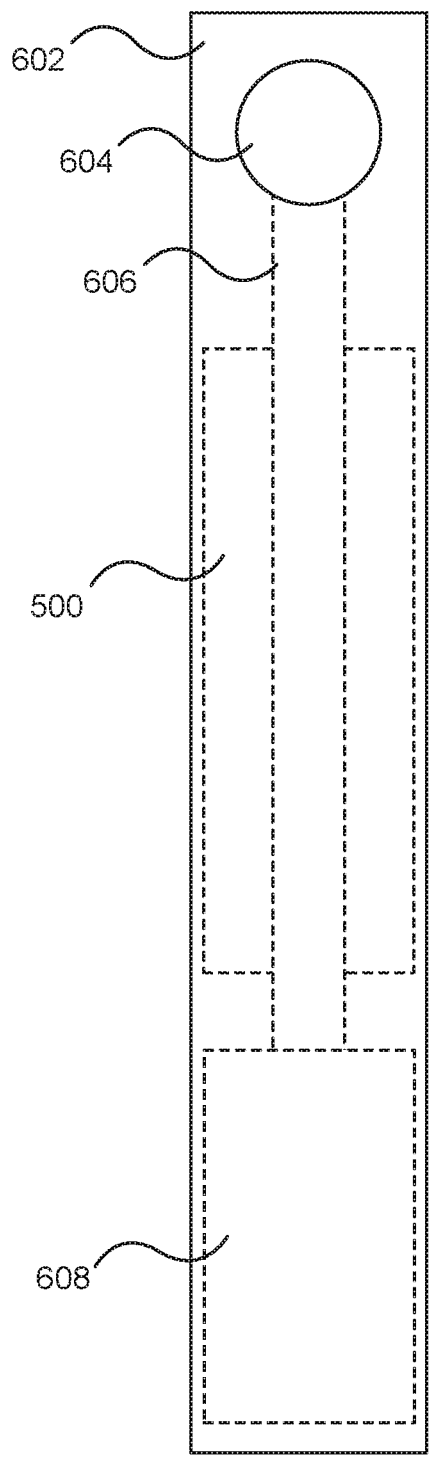
FIG. 6 is a top view illustrating one embodiment of a chip-based biosensor incorporating the array of FIG. 5.

FIG. 6 is a top view illustrating one embodiment of a chip-based biosensor 104 incorporating the array 500 of FIG. 5. In the depicted embodiment, a casing 602 encloses the array 500 on a substrate such as a chip or printed circuit board. The casing 602 may be formed of plastic or another material. A flow channel 606 extends along the transistors of the array 500, from an opening 604 at one end of the casing 602 to an absorbent pad 608 disposed within the casing at the opposite end. In one embodiment, the flow channel 606 is formed in a pressure-sensitive adhesive that couples the array 500 to the casing 602. In another embodiment, the flow channel 606 is formed in a layer of another material, disposed between the array 500 and the top of the casing 602. Thus, a user of the chip-based biosensor may pipette (or otherwise insert) the sample fluid 100 into the opening 604 so that the sample fluid 110 runs along the flow channel 606, over the transistors of the array 500 in sequence, and is absorbed by the absorbent pad. The chip-based biosensor 104 may include pads, leads, or other connectors (not shown) for communication between a chip reader device 102 and the transistors of the array 500.

Figure 7:
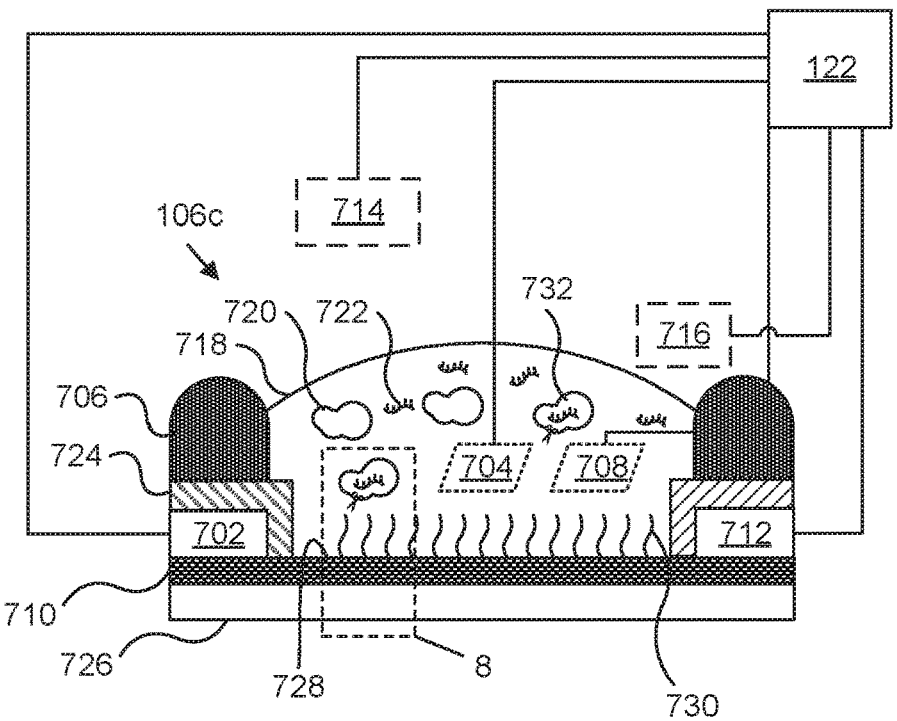
FIG. 7 is a schematic block diagram illustrating a further embodiment of an apparatus for target detection based on collateral cleavage of a reporter by an enzyme, including a further embodiment of a biologically gated transistor.

FIG. 7 is a schematic block diagram illustrating a further embodiment of an apparatus 700 for target detection based on collateral cleavage of a reporter by an enzyme, including a further embodiment of a biologically gated transistor 106c, coupled to a measurement apparatus 122. The biologically gated transistor 106c is depicted in a cross-section view, from the side. The biologically gated transistor 106c and the measurement apparatus 122 in the depicted embodiment may be substantially as described above with reference to FIGS. 1 through 3, and are described further below.

In the depicted embodiment, the biologically gated transistor 106c includes a source 712, a drain 702, a channel 710, a reference electrode 708, a counter electrode 704, and a liquid well 706, which may be substantially as described above. The channel 710, in the depicted embodiment, is a two-dimensional graphene region disposed on a dielectric layer 726 above a substrate (not shown). The source 712 and drain 702 are formed in contact with the channel 710, and are covered by a dielectric 724 (e.g., silicon nitride). A sample fluid 718 (which may be substantially similar to the sample fluid 110 described above) is applied in contact with the surface 728 of the channel 710. For example, the sample fluid 718 may be pipetted (or otherwise inserted) into the liquid well 706 to contact the channel surface 728, the reference electrode 708, and the counter electrode 704. The dielectric 724 electrically insulates the source 712 and drain 702 from the sample fluid 718, so that current between the source 712 and drain 702 is through the channel 710 rather than directly through the sample fluid 718.

In the depicted embodiment, the sample fluid 718 includes a target nucleic acid 722, and an enzyme 720 configured to activate in response to the target nucleic acid to cleave a reporter moiety 730. Enzymes 720 that have not yet encountered or been activated by the target 722 are indicated by a solid outline. Enzymes 732 that have been activated by the target 722 to cleave the reporter are indicated by a copy of the target within the outline of the enzyme 732, indicating that the enzyme 732 is bound to the target, and by a pair of scissors extending from the outline of the enzyme 732, indicating that the collateral cleavage activity of the enzyme has been activated. The enzymes 720 may be added to the sample fluid 718 for detection of the target 722.

With a sufficient concentration of enzymes 720, the rate at which enzymes 720 are activated depends on the presence or concentration of the target 722 within the sample fluid 718. If the target 722 is absent, the enzymes 720 will not be activated. If the target 722 is present at a low concentration, some of the enzymes 720 will be activated and some will not be, and collateral cleavage of the reporters 730 by activated enzymes 732 will occur at a low rate. If the target 722 is present at a higher concentration, more of the enzymes 720 will be activated, and collateral cleavage of the reporters 730 by activated enzymes 732 will occur at a higher rate.

In the depicted embodiment, a reporter moiety 730 (represented by curved lines) is immobilized to the surface 728 of the channel 710. Various types of reporter moieties 730 may be immobilized to a channel surface 728 in various ways. For example, in one embodiment, the channel surface 728 may be functionalized with molecular linkers that include a carboxylic acid functional group and a pyrene base that anchors to a graphene channel 710. Once anchored to the graphene, the carboxylic acid of the linkers may be activated via EDC/NHS chemistry. In a further embodiment, a reporter moiety may be a reporter nucleic acid, which includes a strand of RNA or single-stranded DNA, or a double-stranded DNA oligonucleotide. Nucleotide strands may be modified by the addition of an amine group at one or both ends, to link to the activated carboxylic acid functional group.

In another embodiment, a reporter may be functionalized to bind directly to the channel surface 728 without a linker molecule. In another embodiment, another type of linker molecule or moiety may be used that binds to the reporter on one end and binds to the reporter on another end. Various linkers may include strain alkynes, carboxyl groups, amine groups, imidoesters or N-hydroxysuccinimides (NHS), silane groups, or the like. In some embodiments, a linker end may be conjugated to the channel surface 728 using copper-free click chemistry. In some embodiments, a linker end may include dibenzocyclooctyne-amine (DBCO) or dibutyl octadecylphosphoramidate (DBOP).

In some embodiments, a reporter moiety 730 may include polymeric strands, such as DNA strands, RNA strands, ssDNA strands, strands of sugars in a polysaccharide, strands of other monomers in a polymer, or the like. In one embodiment, strands of a reporter moiety 730 may be linked to the channel surface 728 at one end. In another embodiment, strands of a reporter moiety 730 may be linked to the channel surface 728 at both ends. In some embodiments, a reporter moiety 730 may be immobilized to the channel 710 in the form of a hydrogel formed with strands of the reporter molecule as a backbone of the gel, and the hydrogel may be linked to the channel 710.

Although a reporter moiety 730 is immobilized to the surface 728 of the channel 710 in the depicted embodiment, a channel 710 in another embodiment may be a bare or unfunctionalized channel, and the reporter moiety 730 may be added to the sample fluid 718. With a reporter moiety or molecule 730 in the sample fluid, differences in adsorption of the reporter moiety 730 versus adsorption of cleaved fragments of the reporter moiety 730 to the channel surface may affect an output signal.

The measurement apparatus 122, in the depicted embodiment, is coupled to the source 712, the drain 702, the reference electrode 708, and the counter electrode 704. In various embodiments, the measurement apparatus 122 may apply excitation conditions to the biologically gated transistor 106c via the source 712, the drain 702, and/or the counter electrode 704. In further embodiments, the measurement apparatus 122 may perform measurements of one or more output signals from the biologically gated transistor 106c via the source 712, the drain 702, and/or the reference electrode 708.

In some embodiments, an apparatus 700 may include temperature control circuitry 714, and/or a fluidic device 716. The measurement apparatus 122 may include or communicate with the temperature control circuitry 714, and/or a fluidic device 716, and may control the temperature control circuitry 714, and/or fluidic device 716. FIG. 7 depicts the temperature control circuitry 714 and a fluidic device 716 in dashed lines, indicating that they may be present in some embodiments or absent in other embodiments.

In various embodiments, the measurement apparatus 122 may control a temperature of the sample fluid 718 using temperature control circuitry 714 for various reasons, such as to control, increase, optimize, or decrease a rate at which enzymes 720 are activated by targets 722, or to affect collateral cleavage activity of reporters 730 by activated enzymes 732. Temperature control circuitry 714, in various embodiments, may be any circuitry capable of changing the temperature of the sample fluid 718 and/or the biologically gated transistor 106c. In some embodiments, temperature control circuitry 714 may be capable of heating the sample fluid 718 and/or the biologically gated transistor 106c. In some embodiments, temperature control circuitry 714 may be capable of cooling the sample fluid 718 and/or the biologically gated transistor 106c. In some embodiments, temperature control circuitry 714 may be provided for both heating and cooling.

In various embodiments, temperature control circuitry 714 may include components such as a resistive heater in proximity to the chip-based biosensor 104, a resistive wire on the same substrate as the biologically gated transistor 106c, a Joule heating controller to control the current in a resistive element (or in the channel 710 itself, used as a resistive element for Joule heating), a solid-state heat pump (e.g., using the Peltier effect). In some embodiments, temperature control circuitry 714 may include components for monitoring the temperature of the sample fluid 718 and/or the biologically gated transistor 106c (and for controlling the temperature based on the monitored temperature), such as a thermistor, one or more thermocouples, a silicon bandgap temperature sensor, a resistance thermometer, or the like. Various other or further components for measuring or controlling a temperature may be included as temperature control circuitry 714 in various embodiments of an apparatus 700 or a measurement apparatus 122.

In some embodiments, one or more fluidic devices 716 may be used to drive sample flow through a flow cell or other fluidic or microfluidic channels. In some embodiments, the biologically gated transistor 106c may use a flow cell. However, in some embodiments, the biologically gated transistor 106c may be highly sensitive and may perform high-sensitivity measurements without a flow cell. In some embodiments, a chip-based biosensor 104 may include multiple biologically gated transistors 106c, and a fluidic device 716 may drive flow of a sample fluid over a sequence of biologically gated transistors 106c so that upstream and downstream transistors are, respectively, sensitive to earlier and later aspects of a biochemical interaction occurring at different times.

In various embodiments, the measurement apparatus 122 may apply one or more excitation conditions to the biologically gated transistor 106c, so that one or more output signals from the biologically gated transistor 106c are affected by the excitation conditions and by the state of the reporter moiety 730. In various embodiments, a "state" of a reporter moiety or molecule may be a condition of the moiety or molecule relative to the collateral cleavage activity of activated enzymes. For example, an individual reporter moiety may be in a cleaved or uncleaved state, or may be in a shorter state than an initial cleaved state if an activated enzyme 732 cleaves what remains of an already cleaved reporter. A cleaved state of a single reporter moiety may actually mean that particular copy of the reporter was destroyed or turned into fragments and no longer exists. However, because the term "moiety" is also used herein to refer to multiple copies of the same (or similar) moieties, the state of the collective reporter moiety 730 may be an uncleaved state, a fully cleaved state, or a partially cleaved state where some of the instances or copies of the reporter are cleaved and some are not. Multiple partially cleaved states may be possible with varying degrees of cleavage corresponding to different states.

The state of the reporter moiety 730 may affect an output signal of the biologically gated transistor 106c. For example, an output signal such as a channel-to-liquid capacitance (C response) or a channel current (I response) may depend on whether the reporter was cleaved or not, or on the extent to which cleavage of the reporter occurred. Thus, measurements of affected output signal by the measurement apparatus 122 may be used by the analysis module to determine a parameter relating to the presence of the target nucleic acid 722. Such a parameter may include an indication of whether or not the target nucleic acid 722 is present in the sample fluid 718, a concentration of the target nucleic acid 722 or another parameter corresponding to or related to the concentration, an indication of whether or not (or to what extent) the reporter moiety 730 was cleaved, a determination of the rate of cleavage, or the like.

In various embodiments, the enzyme 720 may be any enzyme configured to activate in response to a target 722 to cleave a reporter. Configuring an enzyme 720 to activate in response to a target 722 to cleave a reporter may involve selecting, engineering, or modifying an enzyme to be activated by the target 722. An enzyme 720 may be selected to have site-specific binding to the target 722, so that the enzyme 720 binds to or is activated by a particular site (such as a DNA or RNA subsequence) within the target 722. Configuring an enzyme 720 to activate in response to a target 722 may include selecting or modifying the enzyme or combining the enzyme with a further component specific to the target. For example, various CRISPR-associated (Cas) enzymes may be guided by guide RNA, and configuring an enzyme 720 to activate in response to a target may include combining the Cas enzyme with guide RNA corresponding to a selected target 722 (e.g., complementary to a sequence, subsequence, or set of subsequences occurring in the target 722). Various ways to configure other or further enzymes 720 such as zinc finger nucleases or TALENS to activate in response to a specific target sequence will be recognized by a skilled person.

In some embodiments, a reporter 730 may be selected based on the collateral cleavage activity of the selected enzyme 720. In some embodiments, however, configuring an enzyme 720 to activate in response to a target 722 to cleave a reporter 730 may further involve selecting, engineering, or modifying an enzyme to have collateral cleavage activity for an already-selected reporter 730. In some embodiments, an enzyme 720 may be selected to have non-specific collateral cleavage activity for the reporter moiety 730. For example, while an enzyme 720 may bind to a specific nucleotide subsequence of a target nucleic acid 722, the enzyme may cleave a reporter nucleic acid without requiring a specific sequence of nucleotides to occur in the reporter. As a further example, if an enzyme has non-specific collateral cleavage activity for ssDNA, any ssDNA sequence may be used as a reporter 730. A length of a reporter 730 (e.g., in base pairs or nucleotides for a DNA or RNA reporter) may be selected without undue experimentation by characterizing the effect of reporter cleavage on output states for different lengths of reporters. An orientation of the reporter 730 relative to the channel 710, in some embodiments, may be controlled or affected by an applied electric field such as a bias applied to the channel 710.

In one embodiment, the enzyme 720 is a nuclease enzyme, and the reporter moiety 730 is a reporter nucleic acid. The reporter nucleic acid may be, or may include RNA, DNA, or single-stranded DNA, and may be selected for immobilization to the channel of the biologically gated transistor based on collateral cleavage activity of the nuclease enzyme. For example, in one embodiment, the target nucleic acid 722 may be double stranded DNA (dsDNA) with a particular sequence, subsequence, or set of subsequences that activates the nuclease enzyme. In a further embodiment, an enzyme for detection of target dsDNA may be a Cas12 enzyme with collateral cleavage activity for ssDNA, and the reporter may thus be an ssDNA moiety.

As a further example, where the target 722 is single-stranded RNA, the enzyme for detection of target ssRNA may be a Cas13 enzyme with collateral cleavage activity for ssDNA, and the reporter may thus be an ssDNA moiety. In another example, where the target 722 is ssDNA, the enzyme for detection of target ssDNA may be a Cas14 enzyme with collateral cleavage activity for ssDNA, and the reporter may thus be an ssDNA moiety. In another example, where the target 722 is viral RNA (double-stranded), the enzyme for detection of viral RNA may be an RNase L enzyme with collateral cleavage activity for ssRNA, and the reporter may thus be an ssRNA moiety. More generally, if an enzyme activated by a target 722 has collateral cleavage activity for some type of molecule or moiety, that type of molecule or moiety may be selected as a reporter 730.

In some embodiments, an enzyme 732 activated by a target 722 may cleave the target 722, and may collaterally cleave the reporter 730. In some embodiments an enzyme that cleaves a target 722 may be modified to bind to the target without cleaving it, and to remain active for collateral cleavage of the reporter 730 while the target is bound to the enzyme.

In some embodiments, a reporter 730 may be any enzyme cleavable molecule. For example, in one embodiment, sugar moieties may be used as reporters 730 in conjunction with an enzyme that has collateral cleavage activity for sugars. In some embodiments, the target 722 may be an enzyme that converts trypsinogen to active trypsin, so that the non-activated enzyme 720 is the trypsinogen and the activated enzyme 732 is the activated trypsin. A reporter cleavable by active trypsin may be a peptide containing at least one arginine and lysine so that cleavage of the peptide by trypsin occurs at the arginine or lysine. Quantification of trypsin activity based on cleavage of the peptide reporter may be useful in tissue culture, cell culture, and proteomics research.

Additionally, although detection of a target is described herein with reference to collateral cleavage of a reporter 730 by an activated enzyme 732, other enzymes may be configured to bind to or otherwise modify a reporter 730 without cleaving it, in response to activation of the enzymes by targets 722. Then, the binding or other modification may similarly be detected by measuring output signals of a biologically gated transistor.

In some embodiments the enzyme 720 may be provided as a reagent for preparation of the sample fluid 718. For example, manual preparation of the sample fluid 718 by a user or automated preparation of the sample fluid 718 by a sample prep apparatus 112 may include addition of the enzyme 720, before or after the sample fluid is applied to the biologically gated transistor 106c. In embodiments where the reporter 730 is not immobilized to the biologically gated transistor 106c the reporter 730 may similarly be added to the sample fluid with the enzyme 720, before or after the sample fluid is applied to the biologically gated transistor 106c. However, if the target 722 is consumable or cleavable by the enzyme, the enzyme (and possibly the reporter) may be added once the sample fluid is already in contact with the biologically gated transistor 106c, so that activation of the enzyme and cleavage of the reporter occurs when it can be sensed via the output signals of the biologically gated transistor 106c.

In some embodiments, the enzyme 720 may be provided preapplied to the biologically gated transistor 106c. For example, a sample fluid that does not contain the enzyme 720 may be applied to a biologically gated transistor 106c to which the enzyme 720 has been preapplied, so that the enzyme 720 mixes into the sample fluid 718.

Figure 8:
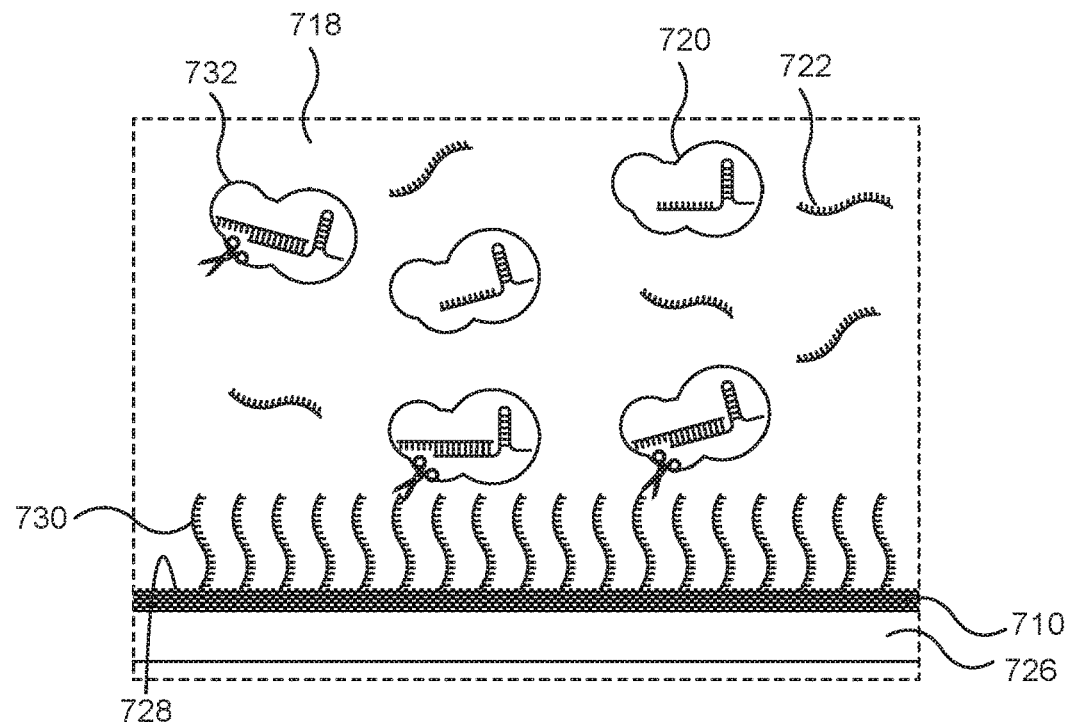
FIG. 8 is a detail view of a region indicated in FIG. 7, illustrating activation of enzymes to cleave a reporter moiety.

FIG. 8 is a detail view of a region outlined in dashed lines in FIG. 7. Portions of the channel 710, channel surface 728, dielectric layer 726, reporters 730, and the sample fluid 718 (including a target 722, non-activated enzymes 720, and activate enzymes 732) are depicted, as described above with reference to FIG. 7.

In the depicted embodiment, the enzyme 720 is an RNA guided Cas enzyme. As depicted, guide RNA corresponds to the target 722. In particular, at least a portion of the guide RNA within the enzymes 720 is complementary to a recognition site in the target nucleic acid 722. In the activated enzymes 732, the recognition site of the target 722 has bound to the guide RNA, and collateral cleavage activity of the enzymes 732 is activated (as indicated by a depiction of scissors) to cleave the reporters 730.

Different guide RNA (or other ways to configure enzymes 720 to activate based on different targets) may be provided in various embodiments, corresponding to different targets. For example, in a test to detect a virus, guide RNA may be provided complementary to a known viral RNA sequence. Similarly, in a test to detect a cancer, guide RNA may be provided complementary to a known cancer miRNA sequence. Detecting enzymatic cleavage of reporters by target-activated enzymes, based on field-effect sensing (e.g., using a biologically gated transistor 106) may provide sensitive target detection with low-cost hardware.

FIGS. 9-14 are side views illustrating a sensing surface 710 such as a channel 710 for a biologically gated transistor or a similar surface for a capacitive or other electrochemical sensor, with various embodiments of reporter moieties before or after collateral cleavage by an enzyme. At the left of FIGS. 9-14, an initial state is depicted for the various reporter moieties, which is also the state in the absence of collateral cleavage (e.g., if the target is not present to activate the enzyme). At the right of FIGS. 9-14, a post-cleavage state is depicted, which occurs after collateral cleavage of the reporter (e.g., if the target is present to activate the enzyme). The enzyme and target as depicted in FIGS. 7 and 8 are not depicted, so as to more clearly see the pre- and post-cleavage states of the reporters. Instead, activation of the enzyme by the target is represented by a depiction of scissors between the pre-cleavage (left) and post-cleavage (right) states.

In some embodiments, a reporter moiety 730 may include polymeric strands, such as DNA strands, RNA strands, ssDNA strands, strands of sugars in a polysaccharide, strands of other monomers in a polymer, or the like, and the strands may be cleavable by an enzyme. In an embodiment depicted in FIG. 9, the reporter moiety 730 includes polymeric strands with first ends linked to the channel 710 and second ends that are not linked to the channel 710. In the configuration where strands have one end linked to the channel, collateral cleavage of the strands by target-activated enzymes results in shortening of the strands, as depicted in the post-cleavage state. Fragments from the non-linked ends may diffuse into the sample fluid or may be removed by rinsing.

Figure 9:
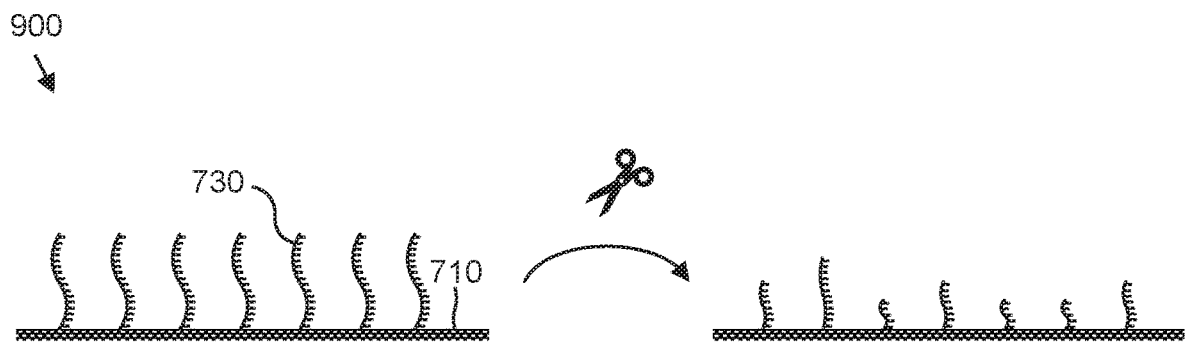
FIG. 9 is a side view illustrating a sensing surface and a reporter moiety before and after cleavage of the reporter, in one embodiment.
Figure 10:
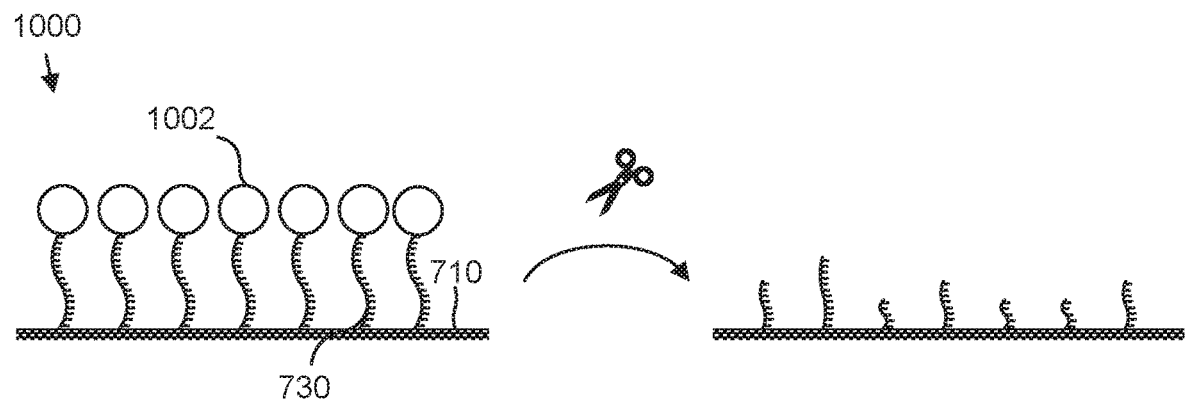
FIG. 10 is a side view illustrating a sensing surface and a reporter moiety before and after cleavage of the reporter, in another embodiment.

In an embodiment depicted in FIG. 10, a reporter moiety includes polymeric strands with first ends linked to the channel 710, as in FIG. 9, but second ends are linked to linkable molecules 1002. Collateral cleavage of the strands by target-activated enzymes results in uncoupling of the linkable molecules 1002 from the channel, to diffuse into the sample fluid or be removed by rinsing. In various embodiments, a linkable molecule 1002 may be any molecule or include any moiety capable of being linked to the second ends of the strands. In some embodiments, the presence or absence of a linkable molecule 1002 near the channel 710 may directly affect an output signal. For example, if the linkable molecule 1002 is a protein with an isoelectric point pH(I) that gives it a nonzero net charge in the sample fluid, then the charge of the protein may affect the channel current, channel capacitance, or other output signals. In some embodiments, a linkable molecule 1002 near the channel 710 may displace ions from the sample fluid, or may be displaced by ions from the sample fluid when the linkable molecule 1002 is unlinked from the channel 710. Thus, even a neutral linkable molecule near the channel may affect the channel 710 differently than the ions it displaces, allowing for target detection based on the linkable molecule 1002.

Figure 11:
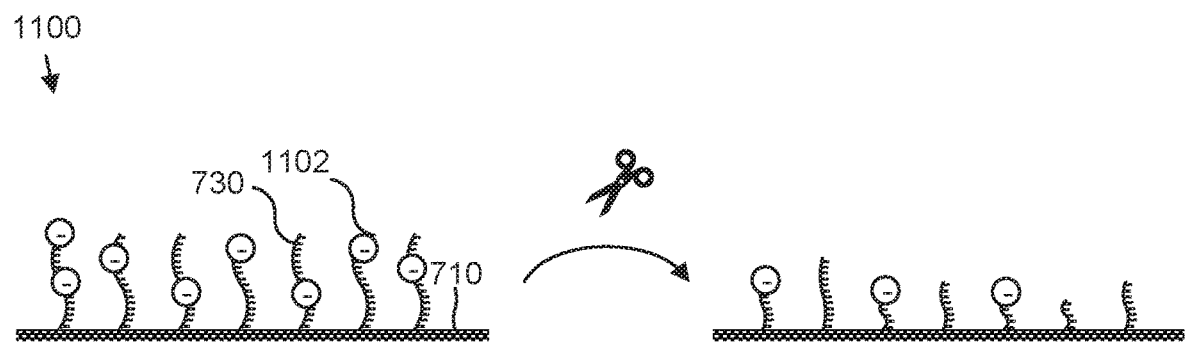
FIG. 11 is a side view illustrating a sensing surface and a reporter moiety before and after cleavage of the reporter, in another embodiment.

In an embodiment depicted in FIG. 11, a reporter moiety 730 is a nucleic acid linked to one or more electroactive moieties 1102. Linkage of the electroactive moieties 1102 to the reporter may occur at the ends of the reporter as in FIG. 10, or along the length of the reporter. Cleavage of the reporter by target-activated enzymes results in uncoupling of the electroactive moieties 1102 from the channel, to diffuse into the sample fluid, be removed by rinsing, or be repelled by a bias applied to the channel 710.

Figure 12:
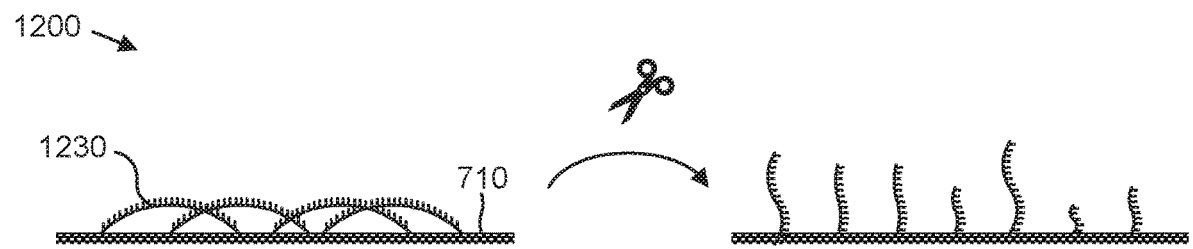
FIG. 12 is a side view illustrating a sensing surface and a reporter moiety before and after cleavage of the reporter, in another embodiment.

In an embodiment depicted in FIG. 12, a reporter moiety 1230 includes polymeric strands similar to the polymeric strands of the reporter moiety 730 described above. However, in the depicted embodiment, the strands include first ends linked to the channel 710 and second ends linked to the channel 710. With the reporter moiety 1230 linked to the channel at both ends, collateral cleavage of the strands by target-activated enzymes results in fragments linked to the channel 710 at one end. In some embodiments, these fragments may extend further away from the channel than when the strands were linked at both ends.

Figure 13:
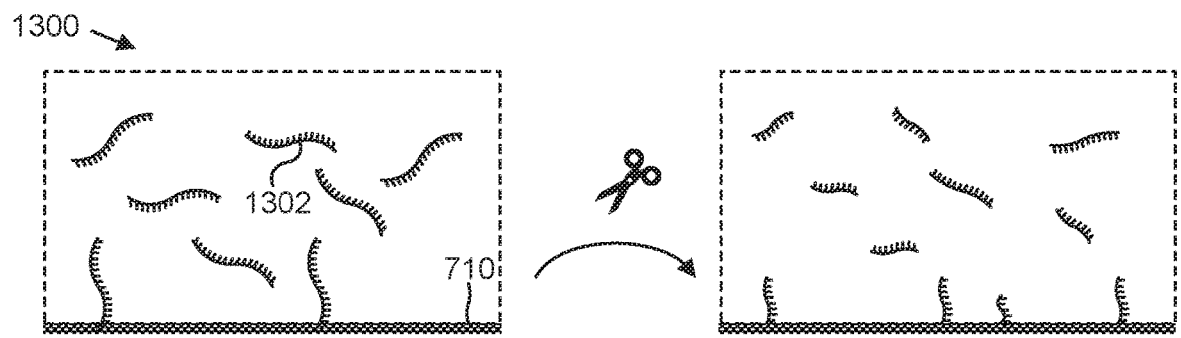
FIG. 13 is a side view illustrating a sensing surface and a reporter moiety before and after cleavage of the reporter, in another embodiment.

In an embodiment depicted in FIG. 13, a reporter moiety 1302 is disposed within the sample fluid rather than being immobilized to the channel 710. However, some copies or instances of the reporter moiety 1302 may adsorb to the channel surface. Collateral cleavage of the reporter moiety 1302 by target-activated enzymes results in smaller fragments within the sample fluid, which may adsorb to the channel surface at a different rate.

Figure 14:
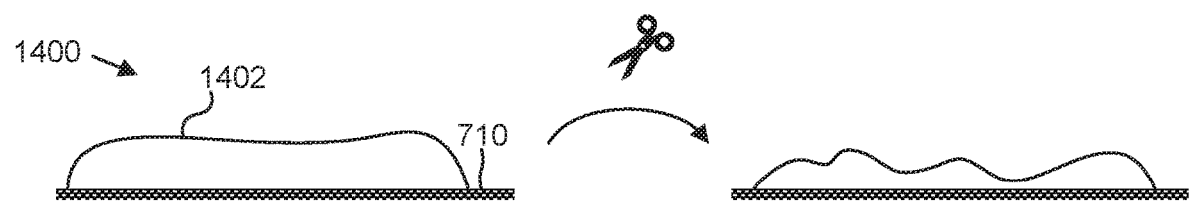
FIG. 14 is a side view illustrating a sensing surface and a reporter moiety before and after cleavage of the reporter, in another embodiment.

In an embodiment depicted in FIG. 14, a reporter moiety is immobilized to the channel as a backbone of a hydrogel 1402 immobilized to the channel 710. A hydrogel may be a network of "backbone" polymer chains, which may be reporter moieties. Cross links between the backbone chains may allow the hydrogel 1402 to admit water from a sample fluid without dissolving in the water. Collateral cleavage of the reporter moiety by target-activated enzymes results in changes to the structure of the hydrogel 1402. For example, cleavage of backbone moieties may degrade the thickness of the hydrogel, or may increase porosity of the hydrogel to admit ions that affect the channel current or capacitance. Thus, the hydrogel is depicted as thinner or degraded in the post-cleavage state.

In the embodiments depicted in FIGS. 9-14 and described above, differences between the pre-cleavage (left) and post-cleavage (right) states of the reporters may affect an output signal for a biologically gated transistor. Affected output signals may include channel capacitance, channel current, electrochemical impedance, or the like.

Figure 15:
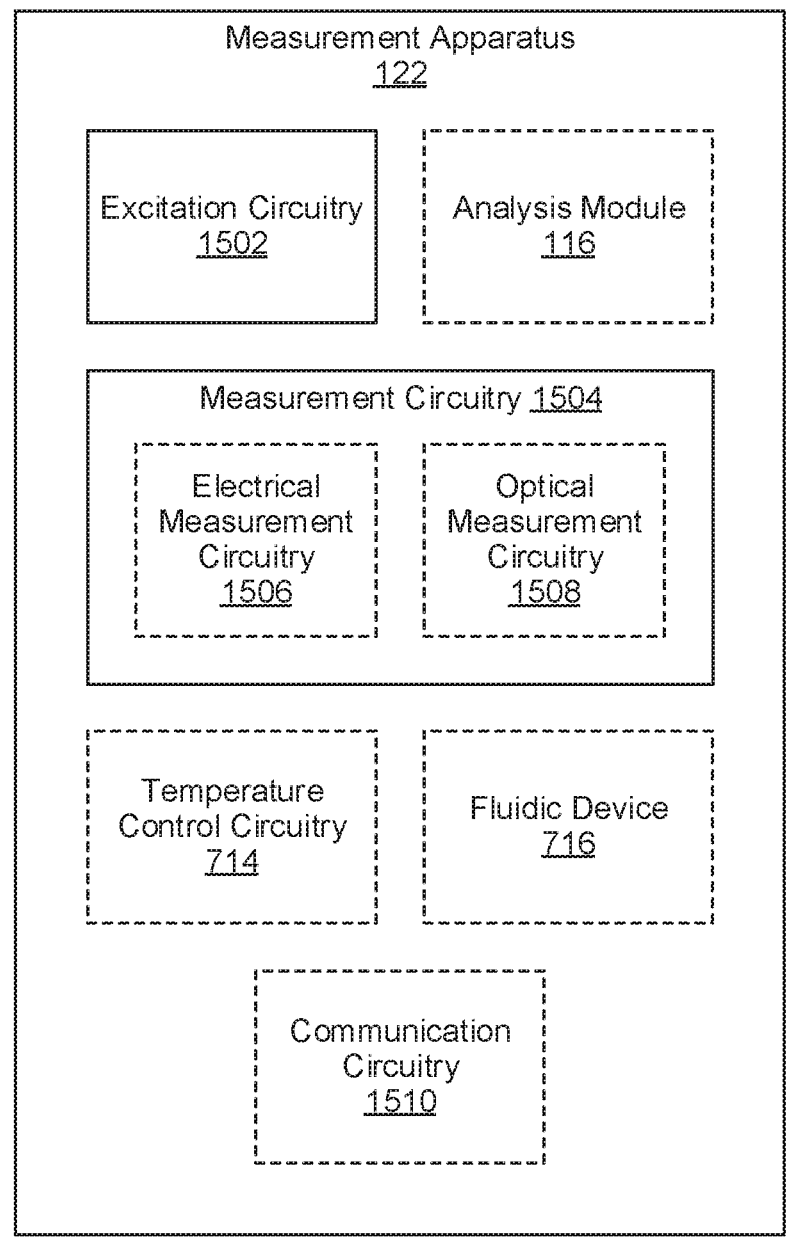
FIG. 15 is a schematic block diagram illustrating one embodiment of a measurement apparatus.

FIG. 15 is a schematic block diagram illustrating one embodiment of an apparatus 1500 for target detection based on collateral cleavage of a reporter by an enzyme, including one embodiment of a measurement apparatus 122. In the depicted embodiment, the measurement apparatus 122 includes excitation circuitry 1502 and measurement circuitry 1504. Certain components indicated by dashed lines in FIG. 15 are included in the depicted embodiment, but may be omitted in another embodiment. In the depicted embodiment, the measurement circuitry 1504 includes electrical measurement circuitry 1506 and optical measurement circuitry 1508. In the depicted embodiment, the measurement apparatus 122 includes an analysis module 116, temperature control circuitry 714, a fluidic device 716, and communication circuitry 1510. The measurement apparatus 122, analysis module 116, temperature control circuitry 714, and fluidic device 716 in the depicted embodiment may be substantially as described above with reference to previous Figures.

In various embodiments, the measurement apparatus 122 may use excitation circuitry 1502 to apply excitation conditions to a biologically gated transistor 106, and may use measurement circuitry 1504 to perform one or more measurements of at least one of the one or more output signals from the biologically gated transistor 106. The output signal(s) may be affected by the excitation conditions, and by the state (e.g., cleaved or uncleaved) of a reporter moiety within a sample fluid 110 applied to the biologically gated transistor 106.

In some embodiments, the measurement apparatus 122 may include an analysis module 116 to determine a parameter relating to presence of a target nucleic acid in the sample fluid, based on the one or more measurements from the measurement circuitry 1504. In some embodiments, however, the measurement apparatus 122 may not include an analysis module 116. For example, in one embodiment an analysis module 116 may be implemented by a computing device 114 separate from the measurement apparatus 122. In some embodiments, the measurement apparatus 122 may include communication circuitry 1510 to transmit the measurements from the measurement circuitry 1504, or information based on the measurements, to a remote data repository 118.

The excitation circuitry 1502, in the depicted embodiment, is configured to apply one or more excitation conditions to a biologically gated transistor 106, or a set of biologically gated transistors 106. An excitation condition, in various embodiments, may be a physical, chemical, or electrical condition applied to biologically gated transistor 106, such as a voltage, amplitude, frequency, amplitude, phase, or waveform for an electrical or electrochemical excitation, a temperature, a fluid flow rate, or the like. Excitation circuitry 1502 may be any circuitry that applies, modifies, removes, or otherwise controls one or more excitation conditions.

In some embodiments, excitation conditions may include one or more electrical signals applied to a biologically gated transistor 106 (or electrochemical potentials applied to the sample fluid), such as constant-voltage biases or time-varying excitation signals. Excitation circuitry 1502 may produce biases or other excitation signals or couple them to the biologically gated transistor 106 (e.g., via a source 212, drain 202, or counter electrode 204). Accordingly, in various embodiments, excitation circuitry 1502 may include any circuitry capable of generating or modulating biases or excitation signals, such as power supplies, voltage sources, current sources, oscillators, amplifiers, function generators, bias tees (e.g., to add a DC offset to an oscillating waveform), a processor executing code to control input/output pins, signal generation portions of source measure units, lock-in amplifiers, network analyzers, chemical impedance analyzers, or the like. Excitation circuitry 1502 in various other or further embodiments may include various other or further circuitry for creating and applying programmable biases.

In some embodiments, excitation conditions may include a temperature for the sample fluid 110 applied to a biologically gated transistor 106, and excitation circuitry 1502 may use temperature control circuitry 714 to control the temperature. Controlling the temperature, in various embodiments, may include increasing or decreasing the temperature (e.g., to detect or analyze temperature-sensitive aspects of a biochemical interaction) maintaining a temperature in a range or near a target temperature, monitoring temperature for feedback-based control, or the like. Thus, as described above, temperature control circuitry 714 may include any circuitry capable of changing the temperature of the sample fluid 110 and/or the biologically gated transistor 106. For example, in various embodiments, temperature control circuitry 714 may include a resistive heater, a Joule heating controller to control current in a resistive heater (or in the channel 210 itself), a solid-state heat pump, a thermistor, or the like. Temperature control circuitry 714 in various other or further embodiments may include various other or further circuitry for controlling or measuring a temperature.

Additionally, in some embodiments, excitation circuitry 1502 may include other or further circuitry, for applying excitation conditions other than or in addition to electrical signals and/or temperature. For example, excitation circuitry 1502 may include electromagnets for magnetic excitation, light emitters of any desired wavelength, radioactive sources, emitters of ultraviolet light, x-rays, gamma rays, electron beams, or the like, ultrasonic transducers, mechanical agitators, or the like. Various other or further types of excitation circuitry 1502 may be used to apply various other or further excitation conditions.

As described above, one or more output signals for a biologically gated transistor 106 may be affected by or sensitive to the state of the reporter moiety, which may be cleaved or uncleaved based on whether an enzyme was activated by a target to cleave the reporter. Where the reporter is immobilized to a channel surface, cleavage of the reporter (and diffusion or rinsing of cleaved fragments away from the surface) can be measured by a change in output signals. Similarly, when the reporter is provided within the sample fluid, cleavage of the reporter (and adsorption of cleaved fragments to the channel surface) may be measured by a change in output signals.

As a simple example, with excitation conditions that include a constant drain-to-source bias voltage, a state of a reporter moiety at or near the channel surface 428 may affect an output signal, such as a drain-to-source current, a capacitance of an ionic double layer formed at the channel surface 428 (e.g., as measured between the drain 202 and the reference electrode 208), or the like. Various output signals that may be affected by the state of the reporter moiety, and measured, may include a complex resistance (e.g., impedance) of the channel 210, electrical current through the channel 210, voltage drop across the channel 210, coupling between the channel 210 and the liquid gate (e.g., biased and/or measured via a counter electrode 204 and/or a reference electrode 208), electrical (channel) and/or electrochemical (liquid gate) voltages, currents, resistances, capacitances, inductances, complex impedances, network parameters (e.g., S-parameters or h-parameters determined using a network analyzer), a Dirac voltage (e.g., a liquid gate voltage that minimizes channel current in a graphene channel 210), charge carrier mobility, contact resistance, kinetic inductance, a spectrum based on multiple measurements such as a power spectral density, an electrical impedance spectrum, an electrochemical impedance spectrum, or the like.

Because certain output signals from the a biologically gated transistor 106 may be affected by the state of a reporter moiety, which may be cleaved or uncleaved based on whether an enzyme was activated by a target to cleave the reporter, information corresponding to the presence of the target can be obtained by measuring one or more of the affected output signals. Thus, in various embodiments, the measurement circuitry 1504 may be configured to perform one or more measurements of the affected output signals. For example, the measurement circuitry 1504 may measure initial and final output signals, output signals for the sample fluid and for a control fluid, or the like. The rate at which the affected output signals properties change indicates the concentration of the target in the sample, with faster rates indicating higher concentrations. The sensitivity of the measurement apparatus 122 may be increased by increasing the length of time between initial and final measurements of the affected output signals.

Additionally, in some embodiments, the measurement circuitry 1504 may be configured to perform a plurality of time-dependent measurements of one or more of the affected output signals. With multiple measurements of affected output signals over time, the analysis module 116 may characterize a parameter relating to the state of the reporter moiety over time. For example, the analysis module 116 may determine the rate at which the reporter is cleaved, which may correspond to the concentration of the target.

Measurement circuitry 1504, in various embodiments, may include any circuitry capable of performing measurements of one or more output signals. For example, in some embodiments, measurement circuitry 1504 may include preamplifiers, amplifiers, filters, voltage followers, data acquisition (DAQ) devices or boards, sensor or transducer circuitry, signal conditioning circuitry, an analog-to-digital converter, a processor executing code to receive and process signals via input/output pins, measurement portions of source measure units, lock-in amplifiers, network analyzers, chemical impedance analyzers, or the like. Measurement circuitry 1504 in various other or further embodiments may include various other or further circuitry for performing measurements of output signals.

In the depicted embodiment, the measurement circuitry 1504 includes electrical measurement circuitry 1506 for performing electrical measurements. Electrical measurements may be measurements of electrical and/or electrochemical output signals. For example, in some embodiments, electrical output signals may be measured via the source 212 and drain 202 terminals of a biologically gated transistor 106. In some embodiments, the measurements include measurements of an electrochemical potential of the sample fluid 110 via a reference electrode 208 of the biologically gated transistor 106.

On a biologically gated transistor 106, a double layer formed by ions in the sample fluid or an optionally added sensitization layer between the graphene channel and the bulk liquid that acts as an effective gate dielectric. A sensitization layer may be an ion-permeable layer with a net charge, so that ions from the fluid may diffuse into the ion-permeable layer of immobilized molecules or moieties due to the Gibbs-Donnan effect, forming a Donnan equilibrium region. In a capacitive or electrochemical sensor other than a transistor, a similar dielectric layer may be formed between a surface (e.g., a surface of a working electrode) and the sample fluid.

Electrical measurement circuitry 1506 may monitor the current through the graphene channel, while excitation circuitry 1502 applies a varying or constant voltage to the liquid gate. The effect of the electric field from the liquid gate is changed by the presence or absence of reporter molecules in the effective gate dielectric region. With reporters immobilized to the channel surface, the catalytic activity of target-activated enzymes driving collateral cleavage slowly removes material from the graphene surface, decreasing the effective dielectric thickness. With reporters in the sample fluid, increased concentration of small pieces of cleaved reporter due to enzyme activity adsorb to the graphene surface, increasing the effective dielectric thickness. In either case, cleavage of the reporters may cause an increase or decrease in current, or capacitance between the channel (or other surface) and the liquid, or a change in the effective gate potential experienced by the graphene (which is equivalent to a shift in the Dirac Voltage). The specific responses depend on the charge and hydrophobicity of the reporter, the effective doping of the channel or other surface, and the properties of the sample fluid. All of this can be done simultaneously by monitoring the channel current in coordination with the applied liquid gate voltage.

Similarly, a surface of a working electrode in an electrochemical system may be used in place of the channel of a biologically gated transistor 106. A working electrode for the electrochemical system may be metal film, a graphite surface, a piece of graphene, or the like. A counter electrode and reference electrode to control and measure the electrochemical potential in the liquid may be provided, as described above. In this measurement, excitation circuitry 1502 may apply a voltage between the liquid and the working electrode with a frequency that varies over time. For example, the frequency may be varied over time to move between 0.1 Hz and 1 MHz. The electrical measurement circuitry 1506 may measure the complex impedance between the working electrode and the liquid, and the capacitance and resistance between the working electrode and the liquid can be calculated. The capacitance between the working electrode and the liquid should increase with increasing thickness of reporter molecules on the surface of the graphene. This is similar to using a biologically gated transistor 106, but with a less complex sensor.

In some embodiments, measurement of electrical signals by electrical measurement circuitry 1506 may include measurement of a current that indicates charge transfer between the sample fluid and the channel of a biologically gated transistor (or a working electrode surface for another electrochemical system). Instead of an impedance spectroscopy measurement, as described in the preceding paragraph, a direct electrochemical measurement may be performed. In this case, the current from the liquid to the channel is measured, where presence of that current indicates charge transfer from the liquid to the channel. A redox label can be added to the sample fluid, such as an Fe(II) salt, that will readily convert to Fe(III) on the surface of channel with the application of a small voltage, resulting in the transfer of an electron from the iron to the channel. By cycling the voltage, the charge transfer is reversed, allowing the iron to be re-used. In this sensor, presence of the reporter molecules on the surface of the channel will lessen the current or completely prevent the current from flowing. If reporter moieties are removed from the surface by cleaving, a higher current indicates enzymatic activity and positive target detection. Conversely, if reporter fragments are adsorbed to the surface after cleaving, a lower current indicates enzymatic activity and positive target detection. In another example, the redox label is included in the reporter, so that very little direct current will be recorded until the reporter is cleaved by the triggered enzyme. After activation of the enzyme by the target, the release of the redox label from the removable reporter will increase the current.

In one embodiment, electrical measurements may be supplemented by optical measurements, and the measurement circuitry 1504 may include optical measurement circuitry 1506 for performing measurements of optical output signals. Optical measurement circuitry 1508, in various embodiments, may include any circuitry capable of detecting or amplifying an optical signal, such as photodiodes, phototransistors, amplifiers, or the like. In one embodiment, one end of a reporter moiety includes or is linked to a fluorophore that will be quenched by proximity to the sensor surface. An example would be a fluorophore that is quenched by proximity to graphene. With reporters immobilized to the channel, activation of an enzyme by a target to cleave a reporter will increase fluorescence as the fluorophores are removed from proximity to the graphene. Conversely, with reporters in the sample fluid, activation of an enzyme by a target to cleave a reporter will decrease fluorescence as reporter fragments containing or linked to the fluorophores are adsorbed to the graphene.

In another embodiment, optical measurement circuitry 1508 may be used to monitor changes in a charge sensitive dye, or to perform surface optical measurements such as surface plasmon resonance or bio-layer interferometry measurements. Such optically measured characteristics may be affected by cleavage of a reporter moiety and thus may be used for target detection. In some embodiments, use of electrical measurement circuitry 1506 and optical measurement circuitry 1508 in the measurement apparatus 122 may allow for correction of errors due to undesired background electrical or optical signals.

Various high frequency excitation and/or measurement techniques may be used to determine additional information. For example, high frequency excitation and/or measurement techniques may be used to detect collateral cleavage of reporters in real time, or to monitor conformational changes of the enzyme in real time as it binds to the target, activates, and cleaves reporters. A variety of suitable high frequency excitation and/or measurement techniques are described in U.S. Provisional Patent Application No. 63/036,772 entitled "DYNAMIC EXCITATION AND MEASUREMENT OF BIOCHEMICAL INTERACTIONS" and filed on Jun. 9, 2020 for Kiana Aran et al., which is incorporated herein by reference.

In various embodiments, portions or components of excitation circuitry 1502 and/or measurement circuitry 1504 may be disposed in a chip-based biosensor 104, a chip reader device 102, or in a separate device (e.g., lab bench test and measurement equipment) coupled to the chip-based biosensor 104. For example, single-use components such as a resistive heater component for excitation circuitry 1502 may be disposed on a chip-based biosensor 104, while multi-use components such a digital signal processing circuitry for generating or analyzing complex waveforms may be disposed in a chip reader device 102. Various other ways to dispose or arrange portions or components of excitation circuitry 1502 and/or measurement circuitry 1504 may be used in various other embodiments.

The analysis module 116, in some embodiments, is configured to determine a parameter relating to presence of the target nucleic acid, based on the one or more measurements performed by the measurement circuitry 1504. Such a parameter may include an indication of whether or not the target nucleic acid 722 is present in the sample fluid 718, a concentration of the target nucleic acid 722 or another parameter corresponding to or related to the concentration, an indication of whether or not (or to what extent) the reporter moiety 730 was cleaved, a determination of the rate of cleavage, or the like. In various embodiments, an analysis module 116 may use various methods, including known quantitative analysis methods to determine a parameter relating to presence of the target nucleic acid, based on the one or more measurements. Results from the analysis module 116, such as parameters characterized by the analysis module 116, may be communicated to a user directly via a display or printout (e.g., from the chip reader device 102), transmitted to a user via data network 120, saved to a storage medium (e.g., in remote data repository 118) for later access by one or more users, or the like.

In some embodiments, an analysis module 116 may be separate from the measurement apparatus 122. For example, an analysis module 116 may be implemented by a computing device 114 separate from the measurement apparatus 122. Thus, in some embodiments, a measurement apparatus 122 may include communication circuitry 1510, instead of or in addition to an analysis module 116. Communication circuitry 1510, in the depicted embodiment, is configured to transmit information to a remote data repository 118. The communication circuitry 1510 may transmit information via the data network 120, and may include components for data transmission (and possibly reception), such as a network interface controller (NIC) for communicating over an ethernet or Wi-Fi network, a transceiver for communicating over a mobile data network, or the like. Various other or further components for transmitting data may be included in communication circuitry 1510 in various other or further embodiments.

In some embodiments, the information transmitted by the communication circuitry 1510 to the remote data repository 118 may be information based on the measurements performed by the measurement circuitry 1504. Information based on the measurements may be the measurements themselves (e.g., raw samples), calculated information based on the measurements (e.g., spectra calculated from the raw data), and/or analysis results (e.g., a determined parameter) from the analysis module 116. In a further embodiment, an analysis module 116 may be in communication with the remote data repository 118 (e.g., via the data network 120). An analysis module 116 may be configured to characterize one or more parameters based on the information transmitted to the remote data repository 118. For example, instead of the analysis module 116 receiving measurements directly from the measurement circuitry 1504, the communication circuitry 1510 may transmit measurements (or information about the measurements) to the remote data repository 118, and the analysis module 116 may retrieve the measurements (or information about the measurements) from the remote data repository 118.

In some embodiments, storing data in a remote data repository 118 may allow information to be aggregated from multiple measurement apparatuses 122 for remote analysis of phenomena that may not be apparent from a single measurement apparatus 122. For example, for epidemiology purposes, a measurement apparatus 122 may determine whether a person is infected with a disease based on a biochemical interaction involving viruses, antibodies, DNA or RNA from a pathogen, or the like, in a sample fluid 110 obtained from the person, which may include a sample of blood, saliva, mucus, cerebrospinal fluid, stool, or the like. Information uploaded to a remote data repository 118 from multiple measurement apparatuses 122 may be used to determine aggregate characteristics, such as how infection rates differ in different geographical regions. In various embodiments, an analysis module 116 may implement various other or further ways of using aggregate information from multiple measurement apparatuses 122

The measurement apparatus 122, in various embodiments, may use excitation circuitry 1502, measurement circuitry 1504, and an analysis module 116 together in various ways with one or more biologically gated transistors 106 to determine or characterize parameters relating to presence of a target. In some embodiments, multiple biologically gated transistors 106 may be homogeneously configured (e.g., for redundancy) or heterogeneously configured (e.g., with channel surfaces 728 functionalized in different ways to characterize different aspects of a biochemical interaction).

In some embodiments, excitation circuitry 1502 and measurement circuitry 1504 may perform a control measurement in parallel with a measurement using a first biologically gated transistor 106. For example, a second biologically gated transistor 106 may be provided in a chip-based biosensor 104, with a non-reactive biomolecule blocking layer or a control fluid such as water instead of the sample fluid 110. The excitation circuitry 1502 and the measurement circuitry 1504 may apply excitations and perform measurements for both transistors 106 in parallel, and the control measurements from the second biologically gated transistor 106 may be subtracted from the measurements from the first biologically gated transistor 106 prior to analysis by the analysis module 116.

In some embodiments, the excitation circuitry 1502 and the measurement circuitry 1504 may apply excitation conditions and perform measurements for multiple transistors 106 with varied conditions. For example, versions of the enzyme or experimental conditions such as buffer composition and temperature may be varied across multiple transistors 106, and the rate of collateral cleavage (or other parameters relating to collateral cleavage or to presence of the target) may be determined and compared. Such a comparison may be an easy way to improve experimental conditions with rapid feedback.

Figure 16:
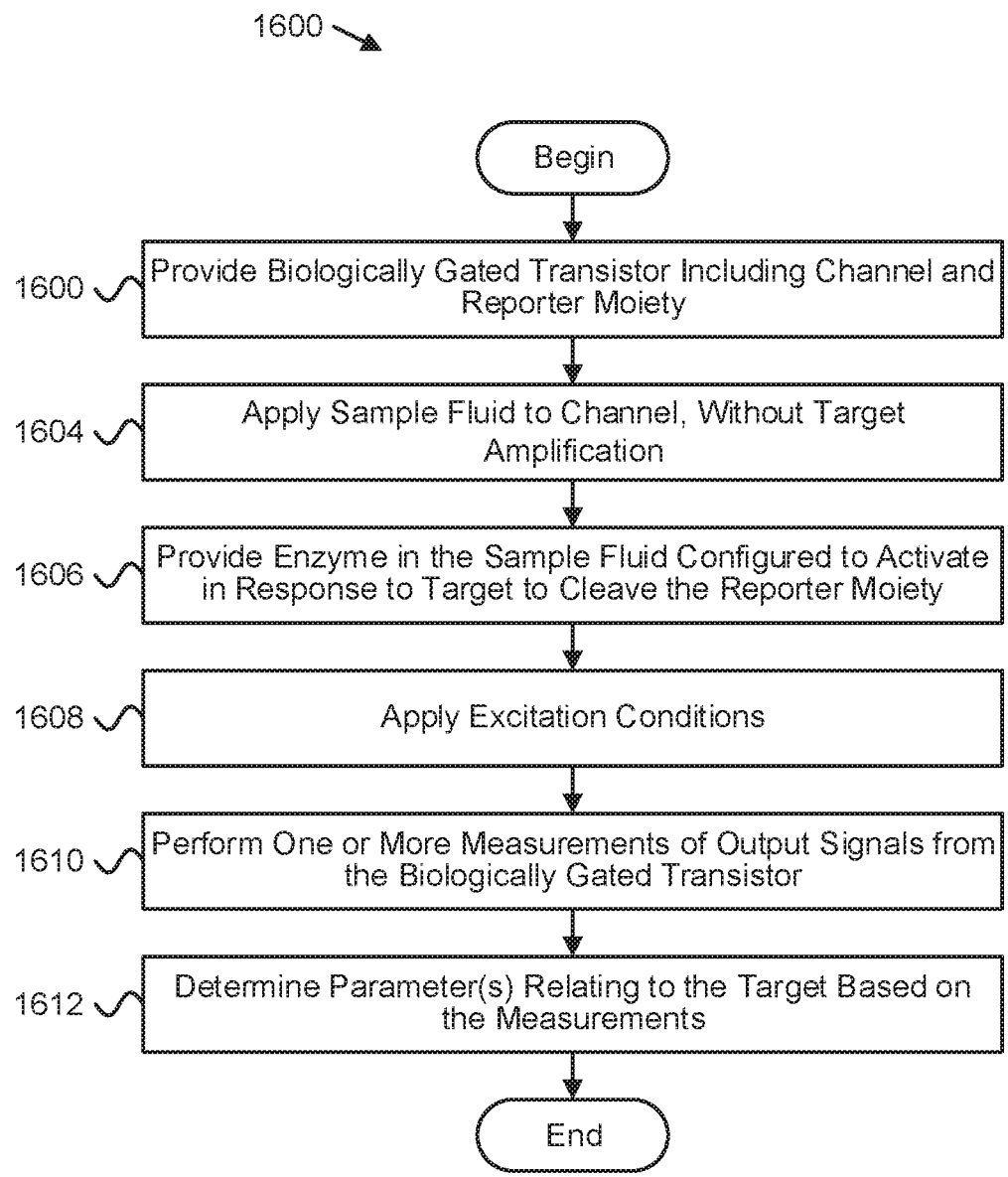
FIG. 16 is a schematic flow chart diagram illustrating one embodiment of a method for target detection based on collateral cleavage of a reporter by an enzyme.

FIG. 16 is a schematic flow chart diagram illustrating one embodiment of a method 1600 for target detection based on collateral cleavage of a reporter by an enzyme. The method 1600 begins with providing 1602 a biologically gated transistor 106 that includes a channel and a reporter moiety immobilized to the channel. A sample fluid is applied 1604 to the channel, without applying a target amplification process to the sample fluid. A target amplification process may be a technique such as recombinase polymerase amplification (RPA), polymerase chain reaction (PCR), or the like, that amplifies a target by making multiple copies of the target. Target amplification may make a low-concentration target easier to detect, but may also obscure information about the original concentration of the target. Thus, sensitivity of a sensor to a non-amplified target may, in various embodiments, increase the speed of tests, and/or provide more information than a sensor used with an amplified target.

An enzyme is provided 1606 within the sample fluid. For example, the enzyme may be provided 1606 by adding the enzyme to the sample fluid or by preapplying the enzyme to the channel before the sample fluid is applied 1604. The enzyme may be configured to activate in response to a target nucleic acid to cleave the reporter moiety.

Excitation circuitry 1502 applies 1608 one or more excitation conditions to the biologically gated transistor so that one or more output signals from the biologically gated transistor 106 are affected by a state of the reporter moiety. Measurement circuitry 1504 performs 1610 one or more measurements of at least one of the one or more output signals from the biologically gated transistor 106 that are affected by the state of the reporter moiety. An analysis module 116 determines 1612 one or more parameters relating to presence of the target nucleic acid, based on the one or more measurements, and the method 1600 ends.

A means for collaterally cleaving a reporter moiety 730, in various embodiments, may include an enzyme selected, engineered or modified to be activated by a target to cleave a reporter other than the target, a nuclease enzyme, an RNA-guided Cas enzyme, a Cas12 enzyme, a Cas13 enzyme, a Cas14 enzyme, an RNase L enzyme, a trypsin enzyme, trypsinogen that converts to active trypsin when activated by a target, or other means disclosed herein. Other embodiments may include similar or equivalent means for collaterally cleaving a reporter moiety 730.

A means for detecting collateral cleavage of a reporter moiety based on an interaction with a surface, in various embodiments, may include one or more chip-based biosensors, capacitive or electrochemical sensors, biologically gated transistors, optical sensors for observing quenching or activation of fluorophores in the reporter based on proximity to a channel surface (or a surface of a capacitive or electrochemical sensor), a redox label that converts between ionization states based on an applied voltage to transfer charge between the surface and the label and back so that a rate of charge transfer is affected by cleavage of the reporter, or the other means disclosed herein. In further embodiments, means for detecting collateral cleavage of a reporter moiety based on an interaction with a surface may include a measurement apparatus 122, measurement circuitry 1504, an analysis module 116, or the like. Other embodiments may include similar or equivalent means for detecting collateral cleavage of a reporter moiety based on an interaction with a surface.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system comprising:
   a biologically gated transistor comprising:
      a channel formed from a two-dimensional material disposed on a dielectric layer of a chip, the two-dimensional material selected from graphene or molybdenum disulfide, wherein an upper surface of the channel is configured to contact a sample fluid;
      a conductive source and a conductive drain that are covered with a dielectric that electrically insulates the conductive source and the conductive drain from the sample fluid so that current between the conductive source and the conductive drain is through the channel; and
      a reporter moiety immobilized to the channel, biologically gated transistor having a liquid gate voltage adjusted via a counter electrode and measured by a reference electrode, and the biologically gate transistor being configured such that one or more output signals of the biologically gated transistor are affected by a state of the reporter moiety at or near the channel surface in response to application of a sample fluid in contact with the channel, the sample fluid comprising an enzyme configured to
         activate, in response to a target nucleic acid, to cleave the reporter moiety;
   excitation circuitry configured to apply adjustments to the liquid gate voltage to the sample liquid via the counter electrode;
   measurement circuitry configured to perform measurements of the one or more output signals from the biologically gated transistor that are modulated by the state of the reporter moiety; and
   an analysis module configured to determine a parameter relating to presence of the target nucleic acid, based on the measurements.

2. The system of claim 1, wherein the reporter moiety comprises polymeric strands with first ends linked to the channel and second ends that are not linked to the channel.

3. The system of claim 2, wherein the second ends are linked to linkable molecules such that in response to the linkable molecules diffusing into the sample fluid in response to the enzyme cleaving the reporter moiety a decrease in an effective thickness of the reporter molecules in channel region and/or a decrease in capacitance of the reporter molecules in the channel region is detected.

4. The system of claim 1, wherein the reporter moiety comprises polymeric strands with first ends linked to the channel and second ends linked to the channel, such that catalytic activity of target-activated enzymes collaterally cleaves the polymeric strands such that cleaved ends of the polymeric strands extend farther away from the channel than when the strands were linked at both ends.

5. The system of claim 1, wherein the reporter moiety is indirectly immobilized to the channel as a backbone of a hydrogel immobilized to the channel.

6. The system of claim 1, wherein the reporter moiety is a reporter nucleic acid and the enzyme is a nuclease enzyme, the reporter nucleic acid comprising one of RNA, DNA, and single-stranded DNA, selected for immobilization to the channel of the biologically gated transistor based on collateral cleavage of the reporter nucleic acid by the nuclease enzyme being activated in response to presence of the target nucleic acid in the sample fluid.

7. The system of claim 1, further comprising the enzyme, wherein prior to application of the sample fluid to the biologically gated transistor, the enzyme is provided as a reagent for preparation of the sample fluid or pre-applied to the biologically gated transistor.

8. The system of claim 7, wherein the enzyme is an RNA-guided Cas enzyme with guide RNA corresponding to a selected target nucleic acid.

9. The system of claim 7, wherein the enzyme is selected to have site-specific binding to the target nucleic acid and non-specific collateral cleavage of the reporter moiety.

10. The system of claim 1, comprising a plurality of biologically gated transistors with the reporter moiety immobilized to channels, wherein:
the plurality of biologically gated transistors comprises the biologically gated transistor;
the excitation circuitry is configured to apply excitation conditions to the plurality of biologically gated transistors;
the measurement circuitry is configured to perform measurements for the plurality of biologically gated transistors; and
the analysis module is configured to determine parameters relating to the plurality of biologically gated transistors.

11. The system of claim 10, wherein the biologically gated transistors are disposed in a two-dimensional array of droplet locations on a substrate.

12. The system of claim 10, wherein the biologically gated transistors are disposed in a linear array of locations on a substrate.

13. The system of claim 1, wherein:
the measurement circuitry is configured to perform a plurality of time-dependent measurements of output signals affected by the state of the reporter moiety; and
the analysis module is configured to characterize a parameter relating to the state of the reporter moiety over time, based on the plurality of time-dependent measurements.

14. The system of claim 1, wherein the set of one or more output signals comprise at least the following: a Dirac voltage, a channel current, a resistance, a capacitance, and/or an effective dielectric thickness of a layer formed at the surface of the channel in response to the state of the reporter moiety.

15. The system of claim 1, wherein the parameter relating to presence of the target nucleic acid comprises one or more of the following: an indication of the presence of the target nucleic acid in the sample fluid, a concentration of the target nucleic acid in the sample fluid, to what extent the reporter moiety was cleaved, and/or a rate of cleavage of the reporter molecule.

16. The system of claim 1, wherein:
the target nucleic acid comprises non-amplified single stranded DNA or non-amplified double stranded DNA;
the enzyme selected for activation by the target nucleic acid comprises a Cas12 enzyme; and
the reporter moiety cleaved by the activated Cas 12 enzyme comprises single stranded DNA.

17. The system of claim 1, wherein:
the target nucleic acid comprises non-amplified RNA;
the enzyme selected for activation by the target nucleic acid comprises a Cas13 enzyme; and
the reporter moiety cleaved by the activated Cas 13 enzyme comprises RNA.

18. The system of claim 1, wherein:
the target nucleic acid comprises non-amplified double stranded viral RNA;
the enzyme selected for activation by the target nucleic acid comprises a RNase L enzyme; and
the reporter moiety cleaved by the activated RNase L enzyme comprises single stranded RNA.

19. The system of claim 1, wherein:
the target nucleic acid comprises a non-amplified cancer microRNA sequence
the enzyme selected for activation by the target nucleic acid comprises a Cas enzyme with a guide RNA complementary to the cancer microRNA sequence; and
the reporter moiety cleaved by the activated Cas enzyme comprises single stranded RNA.

20. The system of claim 19, wherein:
first ends of the reporter moiety cleaved by the activated Cas enzyme are linked to the channel via molecular linkers comprising a carboxylic acid functional group and a pyrene base that anchors to the channel; and
second ends of the reporter moiety cleaved by the activated Cas enzyme are not linked to the channel.

21. The system of claim 11, further wherein for different droplet locations in the two-dimensional array:
channels of the plurality of biologically gated transistors for the different droplet locations are functionalized with the same reporter moiety;
the enzyme in a sample liquid for analysis at the different droplet locations is an RNA-guided Cas enzyme with a guide RNA corresponding to a different target nucleic acids for the different droplet locations;
differences in the parameters determined for the plurality of biologically gated transistors in the different droplet locations are determined in response to differences in the state of the reporter moiety in the different droplet locations in response to activation of the enzyme at the different droplet locations by presence of different target nucleic acids corresponding the guide RNA for the different droplet locations.

* * * * *